(12) United States Patent
Chong et al.

(10) Patent No.: US 9,295,776 B2
(45) Date of Patent: Mar. 29, 2016

(54) RESERVOIR PLUNGER HEAD SYSTEMS AND METHODS

(75) Inventors: Colin A. Chong, Burbank, CA (US); Eric M. Lorenzen, Granada Hills, CA (US); Rafael Bikovsky, Oak Park, CA (US); Arsen Ibranyan, Glendale, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 12/417,976

(22) Filed: Apr. 3, 2009

(65) Prior Publication Data

US 2009/0259198 A1    Oct. 15, 2009

Related U.S. Application Data

(60) Provisional application No. 61/044,269, filed on Apr. 11, 2008.

(51) Int. Cl.
*A61M 5/142*        (2006.01)
*A61B 5/145*        (2006.01)
(Continued)

(52) U.S. Cl.
CPC ........ *A61M 5/14248* (2013.01); *A61B 5/14532* (2013.01); *A61B 5/14865* (2013.01);
(Continued)

(58) Field of Classification Search
CPC ............... A61M 2005/14268; A61M 5/14248; A61M 5/1456; A61M 5/31511; A61M 5/31513; A61M 5/31515; A61M 2005/14573; A61M 2005/1726; A61M 2205/3561; A61M 2205/3569; A61M 2205/3592; A61M 5/143; A61M 5/1452; A61M 5/1723; A61M 5/31501

USPC .............. 604/221, 218, 428, 228, 503, 890.1, 604/93.01; 29/428
See application file for complete search history.

(56) References Cited

U.S. PATENT DOCUMENTS 1,935,494 A    1/1900    West
1,182,042 A    5/1916    Rubin
(Continued)

FOREIGN PATENT DOCUMENTS

DE    23 28 718 A1    1/1975
DE    24 58 004 A1    6/1976
(Continued)

OTHER PUBLICATIONS

International Search Report for Application No. PCT/US2009/038177 dated Jan. 18, 2010.
(Continued)

*Primary Examiner* — Kami A Bosworth
*Assistant Examiner* — Brandy S Lee
(74) *Attorney, Agent, or Firm* — Foley & Lardner LLP

(57) ABSTRACT

A casing may be configured to envelop at least a portion of a plunger arm attached to a plunger head located in a reservoir. A plunger head moveable in a reservoir may have a front portion comprising a first material compatible with fluidic media in an interior volume of the reservoir. A seal member having a first end and a second end that taper to a mid-portion may be positioned between a reservoir and a plunger head. A bias member may be configured to force a plunger arm operatively connected to a plunger head against a drive member to operatively engage the plunger arm to the drive member. A plunger head moveable in a reservoir may have a first ridge, a second ridge, a seal member adjacent at least one of the ridges, and protrusions arranged around at least one of the ridges.

34 Claims, 16 Drawing Sheets

(51) Int. Cl.
*A61B 5/1486* (2006.01)
*A61B 5/00* (2006.01)
*A61M 5/145* (2006.01)
*A61M 5/14* (2006.01)
*A61M 5/172* (2006.01)
*A61M 5/315* (2006.01)

(52) U.S. Cl.
CPC ............ *A61B5/4839* (2013.01); *A61M 5/1452* (2013.01); *A61M 5/1413* (2013.01); *A61M 5/1456* (2013.01); *A61M 5/1723* (2013.01); *A61M 5/31501* (2013.01); *A61M 5/31513* (2013.01); *A61M 2005/14268* (2013.01); *A61M 2005/14573* (2013.01); *A61M 2005/1726* (2013.01); *A61M 2205/3561* (2013.01); *A61M 2205/3569* (2013.01); *A61M 2205/3592* (2013.01); *Y10T 29/49826* (2015.01)

(56) References Cited

U.S. PATENT DOCUMENTS

| | | | |
|---|---|---|---|
| 2,756,748 | A | 7/1956 | Ferguson |
| 3,075,528 | A | 1/1963 | Lundgren et al. |
| 3,886,938 | A | 6/1975 | Szabo et al. |
| 4,363,329 | A | 12/1982 | Raitto |
| 4,911,695 | A | 3/1990 | Lindner |
| 5,830,187 | A * | 11/1998 | Kriesel et al. ............... 604/132 |
| 5,925,732 | A | 7/1999 | Ecker et al. |
| 5,957,889 | A | 9/1999 | Poulsen et al. |
| 6,088,608 | A | 7/2000 | Schulman et al. |
| 6,090,081 | A | 7/2000 | Sudo et al. |
| 6,119,028 | A | 9/2000 | Schulman et al. |
| 6,416,323 | B1 | 7/2002 | Grenfell et al. |
| 6,585,700 | B1 | 7/2003 | Trocki et al. |
| 6,589,229 | B1 | 7/2003 | Connelly et al. |
| 6,740,072 | B2 | 5/2004 | Starkweather et al. |
| 6,827,702 | B2 | 12/2004 | Lebel et al. |
| 7,318,816 | B2 | 1/2008 | Bobroff et al. |
| 7,323,142 | B2 | 1/2008 | Pendo et al. |
| 7,455,663 | B2 | 11/2008 | Bikovsky |
| 7,460,350 | B2 | 12/2008 | Talbot et al. |
| 8,206,353 | B2 | 6/2012 | Chong et al. |
| 8,702,655 | B2 | 4/2014 | Chong et al. |
| 8,858,501 | B2 | 10/2014 | Chong et al. |
| 9,089,637 | B2 | 7/2015 | Chong et al. |
| 2001/0039400 | A1 * | 11/2001 | Lubrecht ............... 604/193 |
| 2001/0041869 | A1 | 11/2001 | Causey, III et al. |
| 2001/0056264 | A1 | 12/2001 | Sayama et al. |
| 2002/0016572 | A1 | 2/2002 | Beebe |
| 2002/0022855 | A1 | 2/2002 | Bobroff et al. |
| 2002/0193679 | A1 | 12/2002 | Malave et al. |
| 2003/0097096 | A1 | 5/2003 | Niedospial, Jr. |
| 2003/0125672 | A1 | 7/2003 | Adair et al. |
| 2003/0170410 | A1 | 9/2003 | Buch-Rasmussen et al. |
| 2003/0212364 | A1 | 11/2003 | Mann et al. |
| 2003/0233075 | A1 | 12/2003 | Huegli |
| 2004/0002682 | A1 | 1/2004 | Kovelman et al. |
| 2004/0028856 | A1 | 2/2004 | Smith et al. |
| 2004/0073095 | A1 | 4/2004 | Causey, III et al. |
| 2005/0020980 | A1 | 1/2005 | Inoue et al. |
| 2005/0043689 | A1 | 2/2005 | Chen |
| 2005/0065760 | A1 | 3/2005 | Murtfeldt et al. |
| 2005/0157024 | A1 | 7/2005 | Silverbrook et al. |
| 2005/0197626 | A1 | 9/2005 | Moberg et al. |
| 2006/0229583 | A1 | 10/2006 | Nagao |
| 2006/0253085 | A1 | 11/2006 | Geismar et al. |
| 2006/0264894 | A1 * | 11/2006 | Moberg et al. ............... 604/503 |
| 2006/0293687 | A1 | 12/2006 | Bogert |
| 2007/0078319 | A1 | 4/2007 | Shah et al. |
| 2007/0219508 | A1 | 9/2007 | Bisegna |
| 2008/0026592 | A1 | 1/2008 | Shah et al. |
| 2008/0039822 | A1 | 2/2008 | Zhang et al. |
| 2008/0050281 | A1 | 2/2008 | Pendo et al. |
| 2008/0051697 | A1 | 2/2008 | Mounce et al. |
| 2008/0051698 | A1 | 2/2008 | Mounce et al. |
| 2008/0051709 | A1 | 2/2008 | Mounce et al. |
| 2008/0051710 | A1 | 2/2008 | Moberg et al. |
| 2008/0051711 | A1 | 2/2008 | Mounce et al. |
| 2008/0051714 | A1 | 2/2008 | Moberg et al. |
| 2008/0051716 | A1 | 2/2008 | Stutz |
| 2008/0051718 | A1 | 2/2008 | Kavazov et al. |
| 2008/0051727 | A1 | 2/2008 | Moberg et al. |
| 2008/0051738 | A1 | 2/2008 | Griffin |
| 2008/0051765 | A1 | 2/2008 | Mounce |
| 2008/0055111 | A1 | 3/2008 | Morgan et al. |
| 2008/0077081 | A1 * | 3/2008 | Mounce et al. ............... 604/67 |
| 2008/0097291 | A1 | 4/2008 | Hanson et al. |
| 2008/0097321 | A1 | 4/2008 | Mounce et al. |
| 2008/0097326 | A1 | 4/2008 | Moberg et al. |
| 2008/0097327 | A1 | 4/2008 | Bente et al. |
| 2008/0097328 | A1 | 4/2008 | Moberg et al. |
| 2008/0097375 | A1 | 4/2008 | Bikovsky |
| 2008/0097381 | A1 | 4/2008 | Moberg et al. |
| 2008/0221509 | A1 | 9/2008 | Gottlieb et al. |
| 2008/0264261 | A1 | 10/2008 | Kavazov et al. |
| 2008/0265859 | A1 | 10/2008 | Talbot et al. |
| 2008/0269680 | A1 | 10/2008 | Ibranyan et al. |
| 2008/0269681 | A1 | 10/2008 | Kavazov et al. |
| 2008/0269682 | A1 | 10/2008 | Kavazov et al. |
| 2008/0269683 | A1 | 10/2008 | Bikovsky |
| 2008/0269687 | A1 | 10/2008 | Chong et al. |
| 2008/0269713 | A1 | 10/2008 | Kavazov |
| 2008/0289300 | A1 | 11/2008 | Gottlieb et al. |
| 2009/0005666 | A1 | 1/2009 | Shin et al. |
| 2009/0030297 | A1 | 1/2009 | Miller et al. |
| 2009/0036870 | A1 | 2/2009 | Mounce et al. |
| 2009/0081753 | A1 | 3/2009 | Shah et al. |
| 2009/0082728 | A1 | 3/2009 | Bikovsky |
| 2009/0098643 | A1 | 4/2009 | Mastrototaro et al. |
| 2009/0163878 | A1 | 6/2009 | Moberg et al. |
| 2009/0171291 | A1 | 7/2009 | Bente, IV et al. |
| 2009/0171324 | A1 | 7/2009 | Chong et al. |
| 2009/0172640 | A1 | 7/2009 | Geismar et al. |

FOREIGN PATENT DOCUMENTS

| | | |
|---|---|---|
| DE | 10 2006 045 959 B3 | 1/2008 |
| EP | 0 110 687 B1 | 10/1986 |
| EP | 0 264 273 B1 | 4/1988 |
| EP | 0 925 798 B1 | 6/1999 |
| EP | 1 293 223 A1 | 3/2003 |
| EP | 1 488 818 A | 12/2004 |
| FR | 1041436 A | 10/1953 |
| FR | 1097841 A | 7/1955 |
| FR | 1104570 A | 11/1955 |
| GB | 0 999 527 | 7/1965 |
| JP | 07-178854 A | 7/1995 |
| JP | 2003-180832 A | 7/2003 |
| WO | WO 85/02256 A | 5/1985 |
| WO | WO-88/05315 A | 7/1988 |
| WO | WO-93/04951 A | 3/1993 |
| WO | WO-00/47254 A1 | 8/2000 |
| WO | WO 01/70307 | 9/2001 |
| WO | WO 2004/030716 A2 | 4/2004 |
| WO | WO 2004/030717 A2 | 4/2004 |
| WO | WO-2006/024650 A2 | 3/2006 |
| WO | WO-2008/024781 A2 | 2/2008 |
| WO | WO-2008/024814 A2 | 2/2008 |
| WO | WO-2009/068251 A1 | 6/2009 |
| WO | WO-2009/126435 A2 | 10/2009 |

OTHER PUBLICATIONS

International Search Report for Application No. PCT/US2009/039714 dated Sep. 21, 2010.
Chinese Office Action with English translation from related Chinese Patent Application No. 200980121959.8, issued Sep. 20, 2012, 18 pages.
U.S. Office Action from related U.S. Appl. No. 13/090,210, mailed Oct. 24, 2012, 7 pages.
U.S. Office Action from related U.S. Appl. No. 12/533,942, mailed Oct. 25, 2012, 8 pages.

(56) References Cited

OTHER PUBLICATIONS

Office Action dated Mar. 28, 2011 from related U.S. Appl. No. 12/547,315.
Search Report dated Mar. 15, 2011 from related PCT Application No. PCT/US2010/044021.
US Office Action dated Jun. 27, 2011 from related U.S. Appl. No. 12/360,077.
US Office Action dated Aug. 29, 2013, from related U.S. Appl. No. 13/090,210.
US Office Action dated Oct. 4, 2013, from related U.S. Appl. No. 12/533,942.
Partial Search Report dated Jan. 12, 2011 from related PCT application No. PCT/US2010/044021.
Search Report dated Feb. 1, 2011 from related PCT application No. PCT/US2010/046530.
US Notice of Allowance dated Jun. 6, 2014, from related U.S. Appl. No. 12/360,077.
US Office Action dated May 19, 2014, from related U.S. Appl. No. 12/533,942.
U.S. Office Action dated Dec. 11, 2014, from related U.S. Appl. No. 12/533,942.
U.S. Notice of Allowance dated May 8, 2015, from related U.S. Appl. No. 12/533,942.
US Notice of Allowance dated Dec. 19, 2013, from related U.S. Appl. No. 13/090,210.
US Office Action dated Nov. 28, 2011, from related U.S. Appl. No. 12/547,315.
US Office Action dated Apr. 24, 2012, from related U.S. Appl. No. 12/533,942.

* cited by examiner

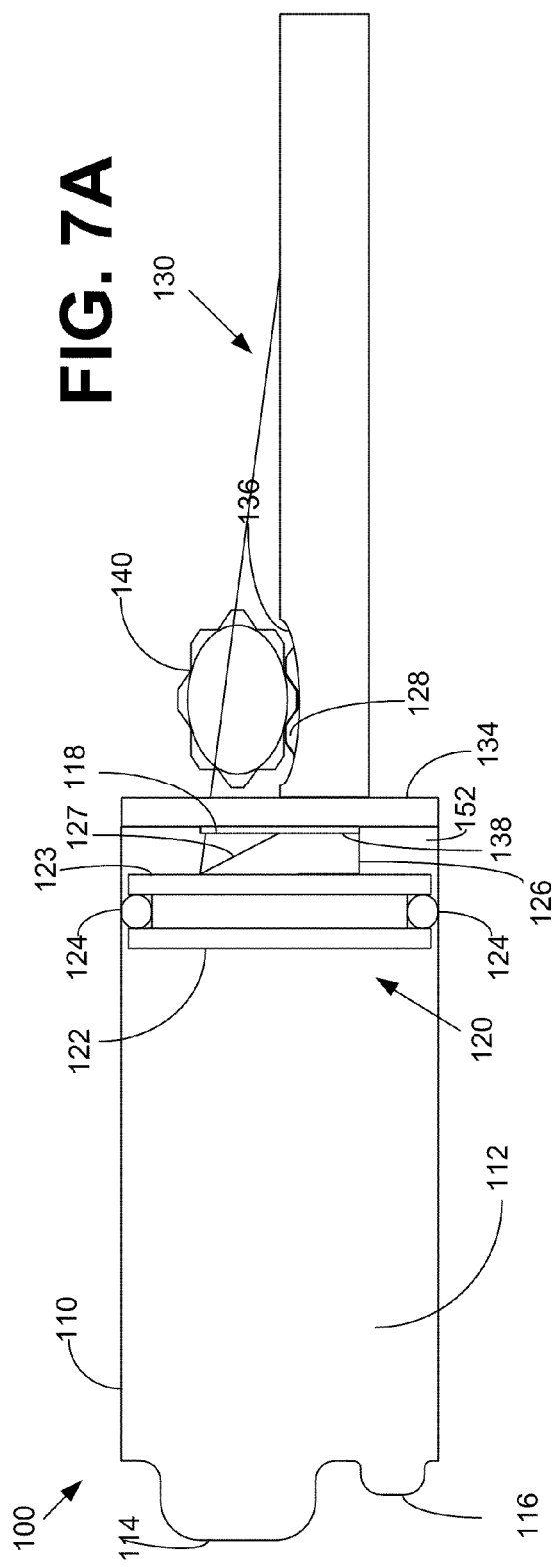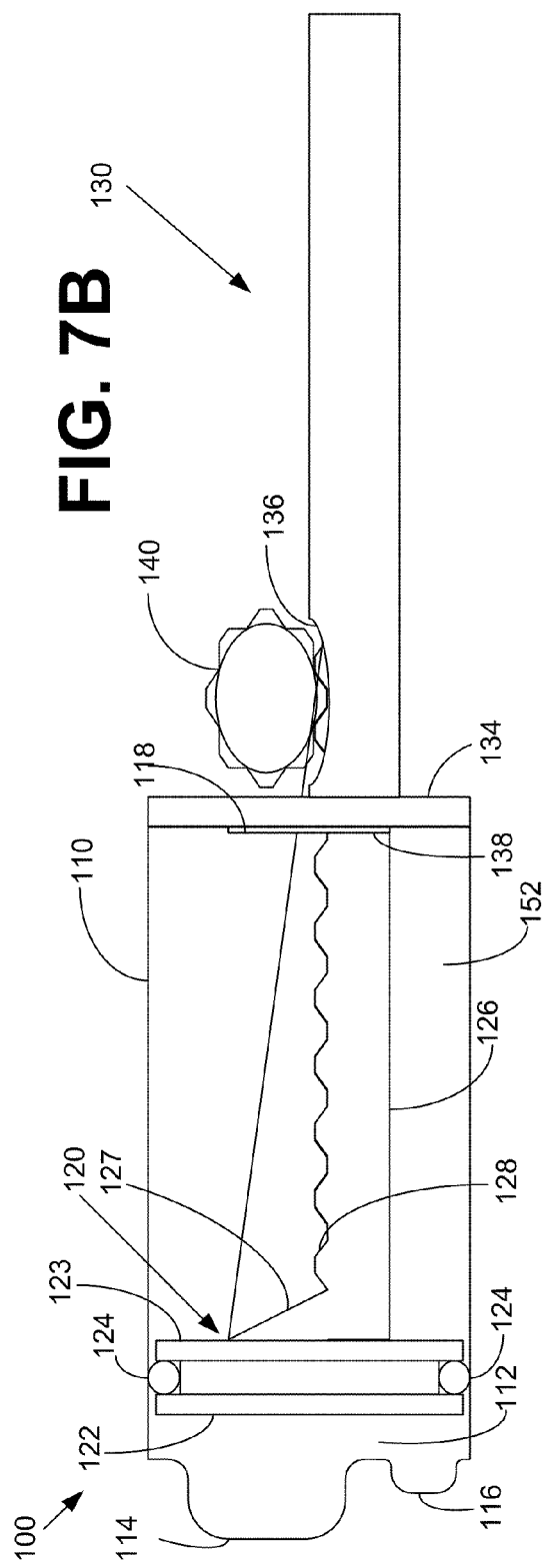

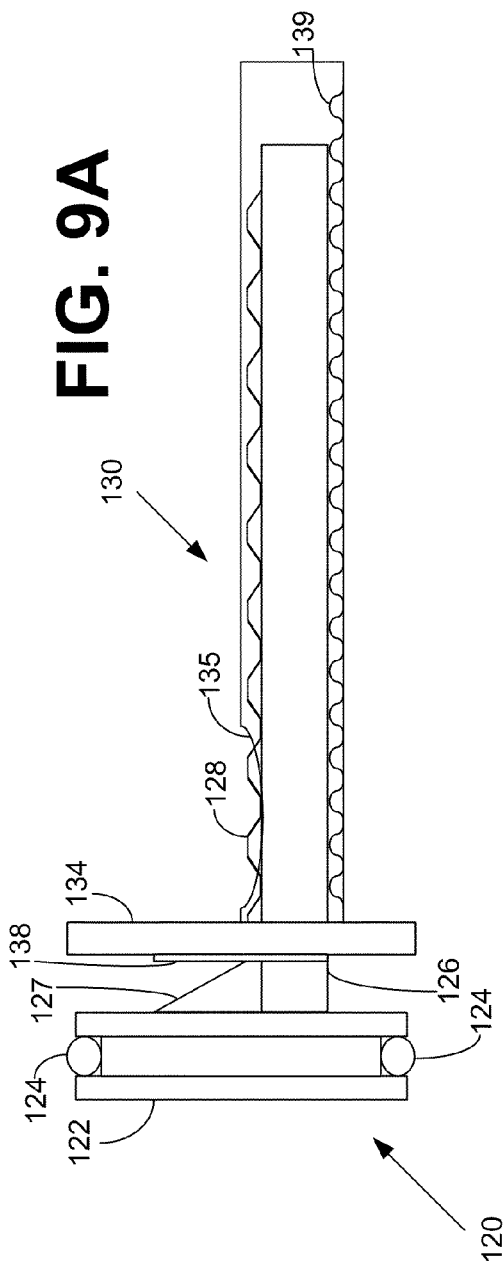
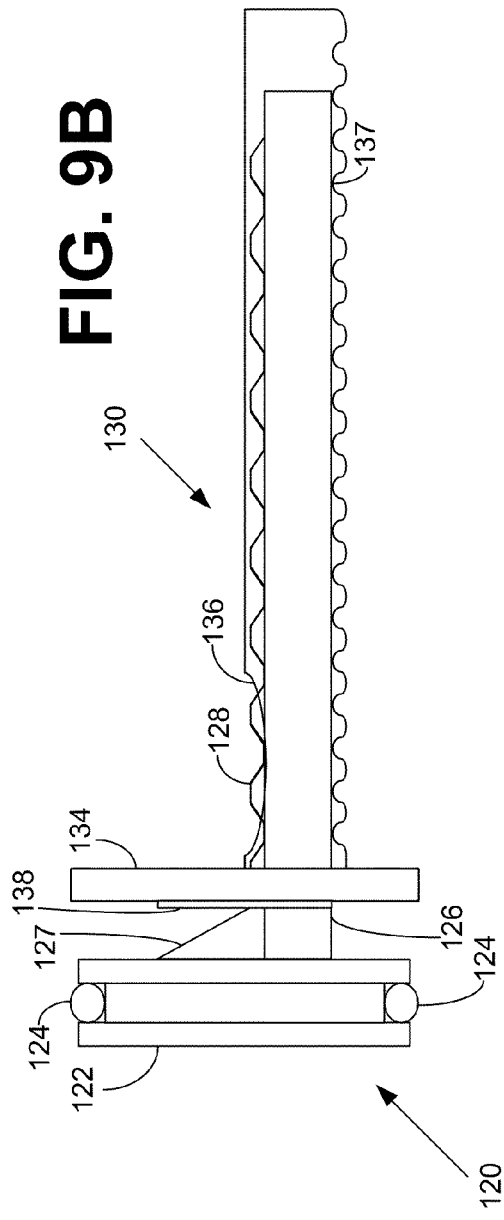

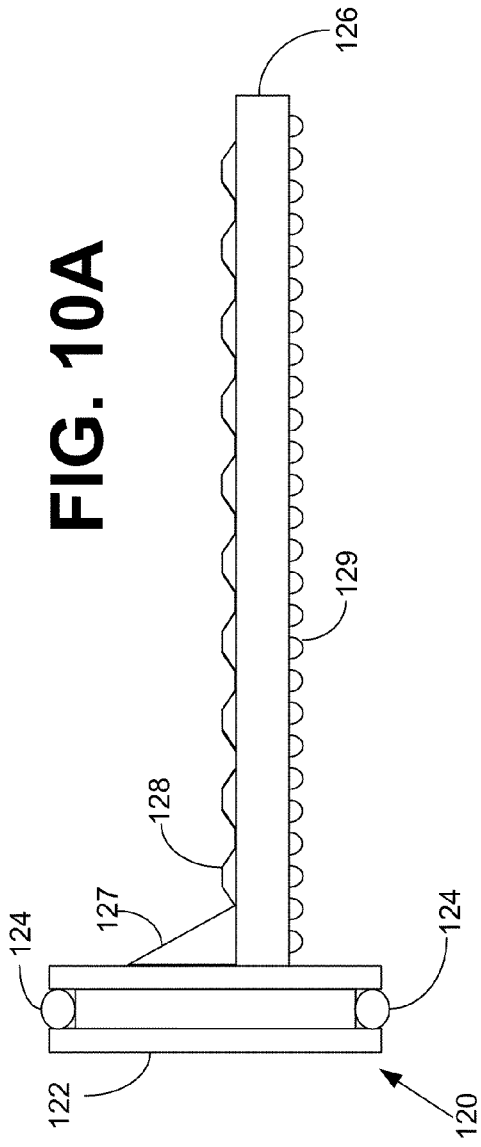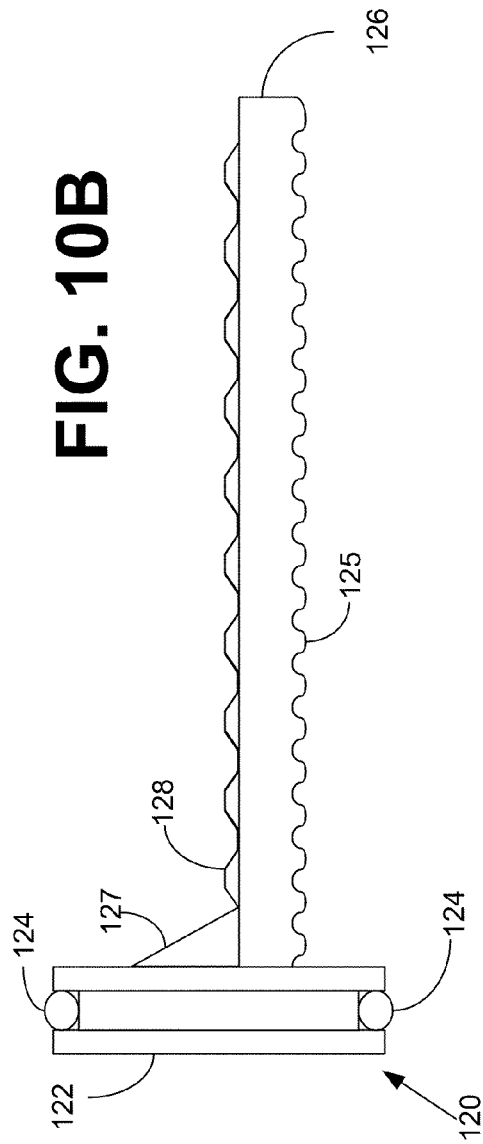

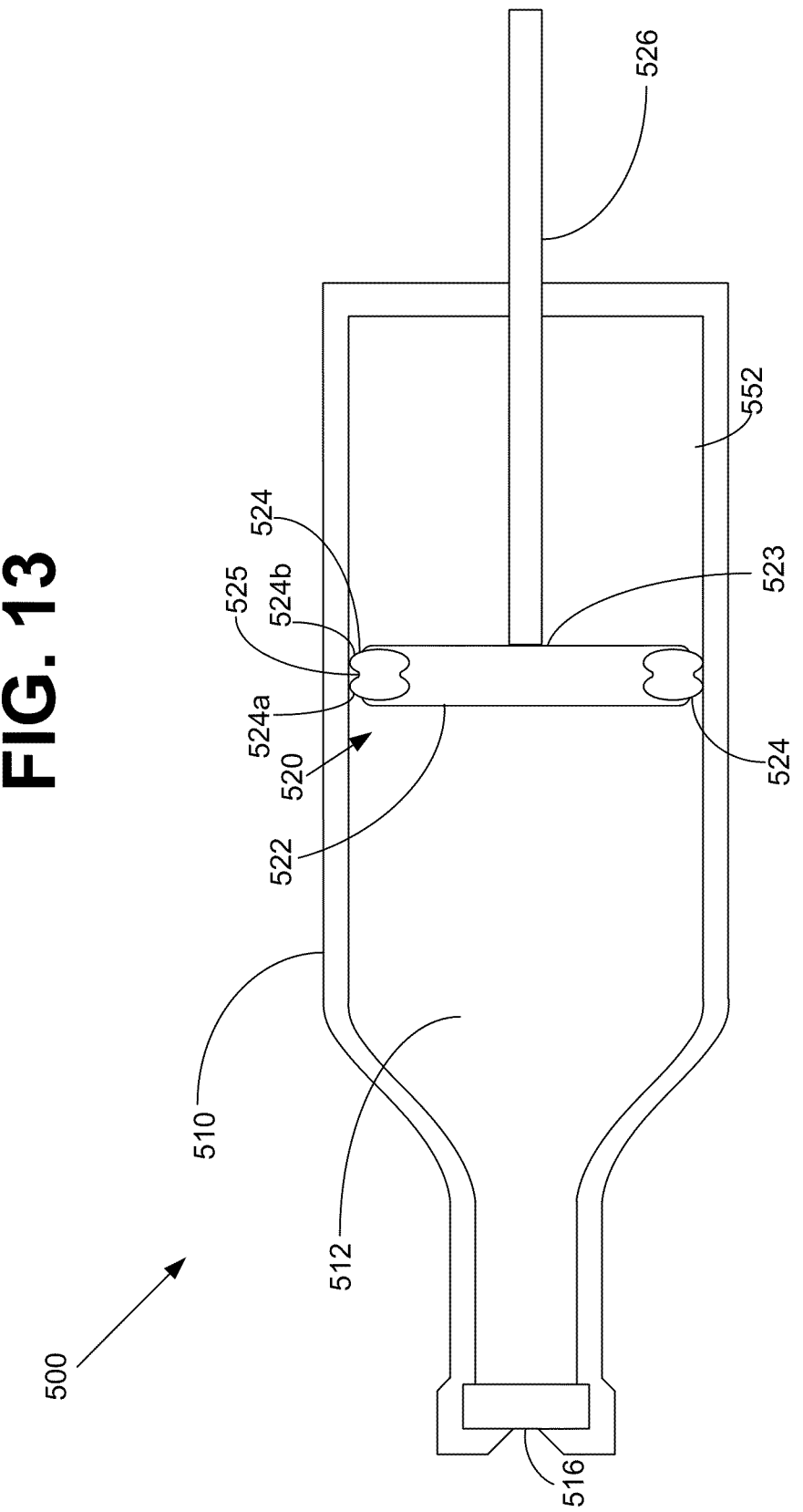

RESERVOIR PLUNGER HEAD SYSTEMS AND METHODS

CROSS-REFERENCE TO RELATED PATENT APPLICATIONS

This application claims priority from Provisional Application U.S. Application 61/044,269, filed Apr. 11, 2008, incorporated herein by reference in its entirety.

BACKGROUND

1. Field of the Invention

Embodiments of the present invention relate generally to systems and methods that include reservoirs for containing fluidic media and having movable plungers and, in specific embodiments, to infusion medium delivery systems and methods employing such reservoirs.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may contain reservoirs of fluidic media, such as, but is not limited to, insulin. External pump type delivery devices may be connected in fluid flow communication to a patient or user-patient, for example, through a suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a user-patient, for example, through a suitable hollow tubing. The hollow tubing may be connected to a hollow needle that is designed to pierce the user-patient's skin and deliver an infusion medium to the user-patient. Alternatively, the hollow tubing may be connected directly to the user-patient as or through a cannula or set of micro-needles.

In contexts in which the hollow tubing is connected to the user-patient through a hollow needle that pierces the user-patient's skin, a manual insertion of the needle into the user-patient can be somewhat traumatic to the user-patient. Accordingly, insertion mechanisms have been made to assist the insertion of a needle into the user-patient, whereby a needle is forced by a spring to quickly move from a retracted position into an extended position. As the needle is moved into the extended position, the needle is quickly forced through the user-patient's skin in a single, relatively abrupt motion that can be less traumatic to certain user-patients as compared to a slower, manual insertion of a needle. While a quick thrust of the needle into the user-patient's skin may be less traumatic to some patient's than a manual insertion, it is believed that, in some contexts, some patients may feel less trauma if the needle is moved a very slow, steady pace. Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

As compared to syringes and insulin pens, pump type delivery devices can be significantly more convenient to a user-patient, in that accurate doses of insulin may be calculated and delivered automatically to a user-patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and as doctors and user-patients become more familiar with such devices, the popularity of external medical infusion pump treatment increases and is expected to increase substantially over the next decade.

SUMMARY OF THE DISCLOSURE

A system for transferring fluidic media in accordance with an embodiment of the present invention may include, but is not limited to, a reservoir body, a plunger head, a plunger arm, and a casing. The reservoir body may have an interior volume for containing fluidic media. The plunger head may be moveable in an axial direction within the reservoir body. The plunger arm may be operatively connected to the plunger head. The casing may extend from the reservoir body. The casing may allow the plunger arm to move in the axial direction relative to the reservoir body to move the plunger head in the axial direction within the reservoir body.

In various embodiments, the plunger arm may have at least one side adjacent the casing and at least partially supported by the casing to align the plunger arm for movement in the axial direction relative to the reservoir body.

In various embodiments, the plunger arm may have an arm portion for operatively engaging a drive member configured to move the plunger arm and the plunger head relative to the reservoir body when the arm portion is operatively engaged to the drive member. In some embodiments, the casing may have an opening for allowing the arm portion of the plunger arm to operatively engage the drive member through the opening.

In various embodiments, the system may further comprise a plurality of protuberances positioned on a surface of the plunger arm. The protuberances on the surface of the plunger arm may be for contacting an interior surface of the casing.

In various embodiments, the plunger arm may have a surface having concavities and convexities. The convexities on the surface of the plunger arm may be for contacting an interior surface of the casing.

In various embodiments, the system may further comprise a plurality of protuberances positioned on an interior surface of the casing. The protuberances on the interior surface of the casing may be for contacting the plunger arm.

In various embodiments, the casing may have an interior surface having concavities and convexities. The convexities on the interior surface of the casing may be for contacting the plunger arm.

In various embodiments, the system may further comprise a support flange having a first side and a second side. The first side of the support flange may be connected to a side of the plunger arm. The second side of the support flange may be connected to a surface of the plunger head that is operatively connected to the plunger arm.

A method of making a system for transferring fluidic media in accordance with an embodiment of the present invention may include, but is not limited to any one or combination of, (i) providing a reservoir body having an interior volume for containing fluidic media, (ii) locating a plunger head moveable in an axial direction within the reservoir body, (iii) operatively connecting a plunger arm to the plunger head, and (iv) extending a casing from the reservoir body to allow the plunger arm to move in the axial direction relative to the reservoir body to move the plunger head in the axial direction within the reservoir body.

A system for transferring fluidic media in accordance with an embodiment of the present invention may include, but is not limited to, a reservoir and a plunger head. The reservoir may have an interior volume for containing fluidic media. The plunger head may be moveable in an axial direction within the reservoir. The plunger head may comprise a front portion and a rear portion. The front portion may be in contact with fluidic media when fluidic media is in the interior volume of the reservoir. The front portion may comprise a first material compatible with fluidic media in the interior volume of the reservoir. The rear portion may be located on an opposite side of the plunger head from the interior volume of the reservoir. The rear portion may be connectable to a plunger arm. The rear portion may comprise a second material different from the first material.

In various embodiments, the system may further comprise a seal member positioned between the reservoir and the plunger head. In some embodiments, the seal member may be positioned between the front portion and the rear portion of the plunger head.

In various embodiments, the system may further comprise a connection structure that removably attaches the front portion of the plunger head to the rear portion of the plunger head and allows removal of the front portion of the plunger head from the rear portion of the plunger head. In various embodiments, the second material may be incompatible with fluidic media in the interior volume of the reservoir.

A method of making a system for transferring fluidic media in accordance with an embodiment of the present invention may include, but is not limited to any one or combination of, (i) providing a reservoir having an interior volume for containing fluidic media, and (ii) locating a plunger head moveable in an axial direction within the reservoir, the plunger head comprising a front portion in contact with fluidic media when fluidic media is in the interior volume of the reservoir, the front portion comprising a first material compatible with fluidic media in the interior volume of the reservoir and a rear portion located on an opposite side of the plunger head from the interior volume of the reservoir, the rear portion connectable to a plunger arm, the rear portion comprising a second material different from the first material.

A system for transferring fluidic media in accordance with an embodiment of the present invention may include, but is not limited to, a plunger head, and a seal member. The plunger head may be movable in an axial direction within a reservoir for containing fluidic media. The seal member may be arrangeable between the reservoir and the plunger head for movement with the plunger head. The seal member may have a first end and a second end. The first end and the second end of the seal member may taper to a mid-portion.

In various embodiments, the mid-portion of the seal member may have a narrower dimension relative to each of the first and second ends of the seal member. In various embodiments, the first end and the second end of the seal member may be substantially round. In various embodiments, the first end and the second end of the seal may be aligned with each other in the axial direction.

In various embodiments, a space may be formed between the mid-portion of the seal member and the reservoir. In further embodiments, the first end and the second end of the seal may be in contact with the reservoir. In yet further embodiments, the first end and the second end of the seal may be in contact with the reservoir as the plunger head moves in the axial direction within the reservoir body.

A method of making a system for transferring fluidic media in accordance with an embodiment of the present invention may include, but is not limited to any one or combination of, (i) locating a plunger head moveable in an axial direction within a reservoir for containing fluidic media, and (ii) positioning a seal member between the reservoir and the plunger head for movement with the plunger head, the seal member having a first end and a second end, the first end and the second end of the seal member tapering to a mid-portion.

A system for transferring fluidic media in accordance with an embodiment of the present invention may include, but is not limited to, a plunger arm and a bias member. The plunger arm may be operatively connectable to a plunger head that is moveable within a reservoir. The plunger arm may have an arm portion that is configured for operative engagement to a drive member configured to move the plunger arm and the plunger head when the arm portion of the plunger arm is operatively engaged to the drive member. The bias member may be configured to force the plunger arm against the drive member to operatively engage the plunger arm to the drive member.

In various embodiments, the system may further comprise a casing configured to support the plunger arm and to envelop at least a portion of the plunger arm. In some embodiments, the bias member may be positioned between the casing and the plunger arm. In some embodiments, the casing may have an opening for allowing the arm portion of the plunger arm to operatively engage the drive member.

In various embodiments, the system may further comprise an outer casing configured to enclose the drive member and at least a portion of the plunger arm. In some embodiments, the bias member may be positioned between the outer casing and the plunger arm.

A method of making a system for transferring fluidic media in accordance with an embodiment of the present invention may include, but is not limited to any one or combination of, (i) providing a plunger arm operatively connectable to a plunger head that is moveable within a reservoir, the plunger arm having an arm portion that is configured for operative engagement to a drive member configured to move the plunger arm and the plunger head when the arm portion of the plunger arm is operatively engaged to the drive member and (ii) providing a bias member configured to force the plunger arm against the drive member to operatively engage the plunger arm to the drive member.

A system for transferring fluidic media may include, but is not limited to, a plunger head, a seal member, and a plurality of protrusions. The plunger head may be moveable in an axial direction within a reservoir for containing fluidic media. The plunger head may have a first ridge and a second ridge. The seal member may be arranged adjacent at least one of the first ridge and the second ridge. The seal member may be in contact with the reservoir. The plurality of protrusions may be arranged around at least one of the first ridge and the second ridge.

In various embodiments, the protrusions may be for limiting lateral movement of the plunger head relative to the reservoir. In various embodiments, the seal member may be arranged between the first ridge and the second ridge. In various embodiments, the plunger head may have a groove for containing at least a portion of the seal member. In various embodiments, a space may be provided between each of the protrusions and the reservoir. In various embodiments, the first ridge and the second ridge may be separate and spaced apart.

BRIEF DESCRIPTION OF THE DRAWINGS

FIGS. 7A and 7B illustrate a cross-section of a system for transferring fluidic media in accordance with an embodiment of the present invention;

FIG. 9A illustrates a cross-section of a portion of a system for transferring fluidic media in accordance with an embodiment of the present invention;

FIG. 9B illustrates a cross-section of a portion of a system for transferring fluidic media in accordance with an embodiment of the present invention;

FIG. 10A illustrates a cross-section of a portion of a system for transferring fluidic media in accordance with an embodiment of the present invention;

FIG. 10B illustrates a cross-section of a portion of a system for transferring fluidic media in accordance with an embodiment of the present invention;

FIG. 13 illustrates a cross-section of a system for transferring fluidic media in accordance with an embodiment of the present invention;

DETAILED DESCRIPTION

Figure 1:
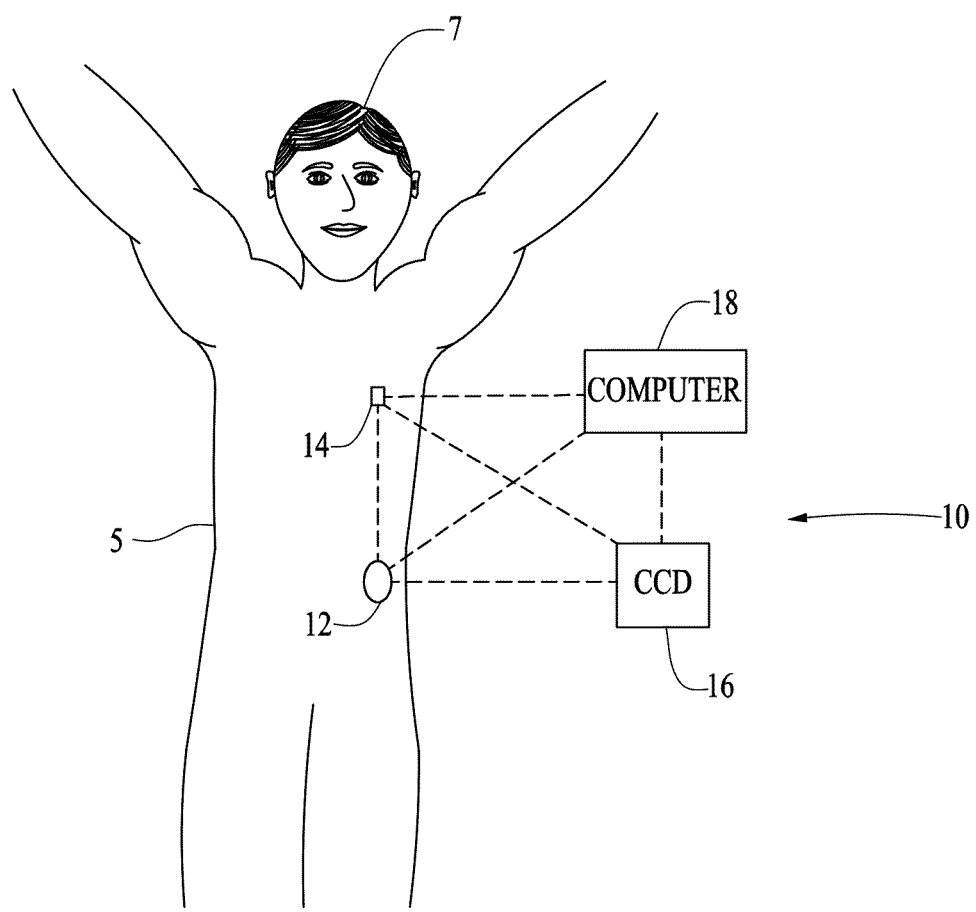
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No.

11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S.

patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
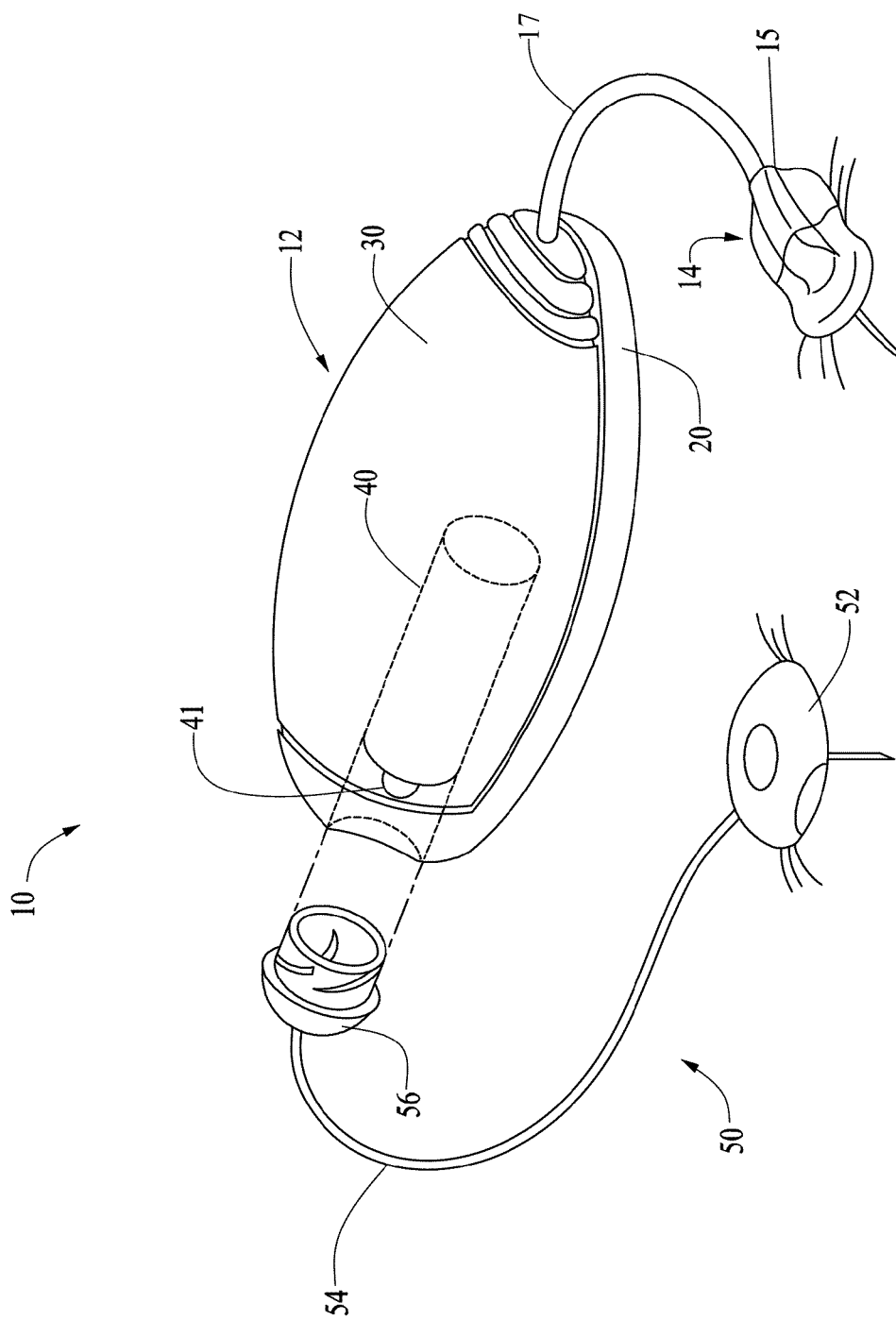
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient, to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 includes a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. In addition, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) within the reservoir system 40. The electrically driven motor may drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
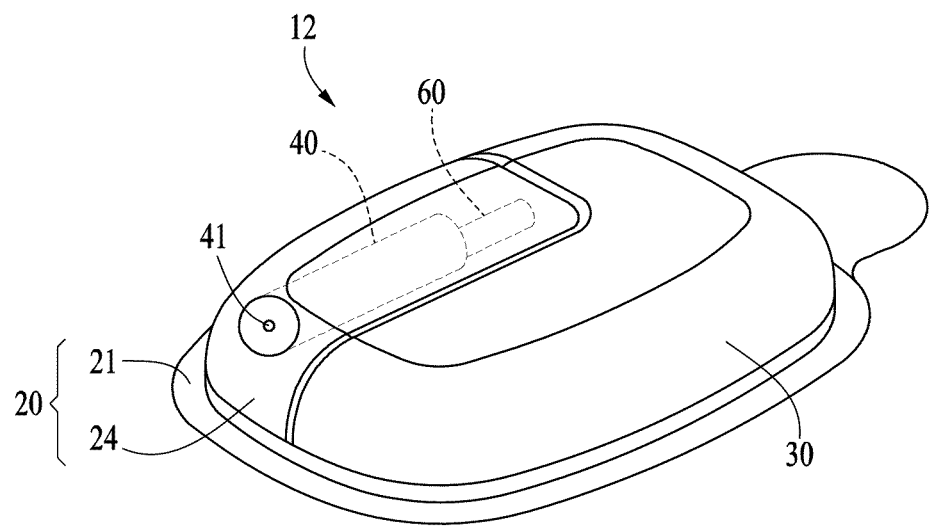
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
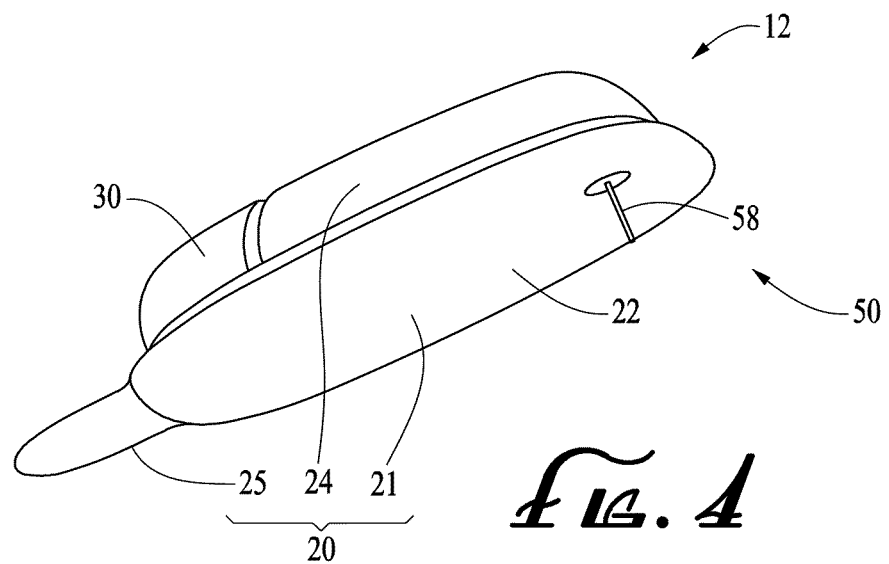
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed; leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

Figure 5A:
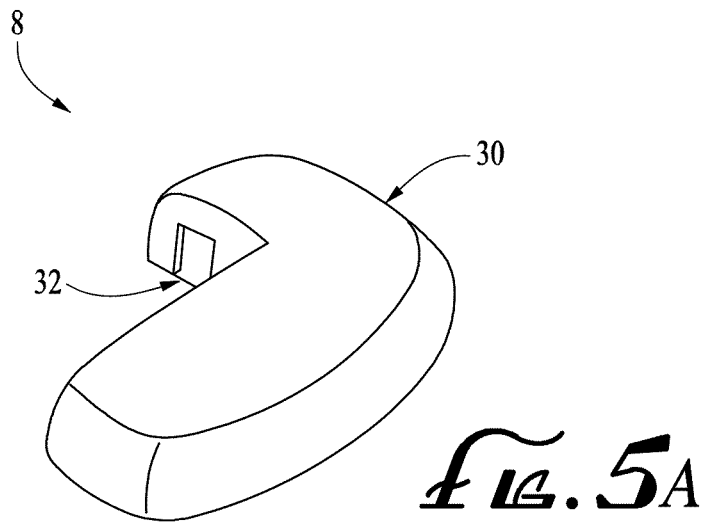
FIG. 5A illustrates a durable portion of a delivery device in accordance with an embodiment of the present invention.
Figure 5B:
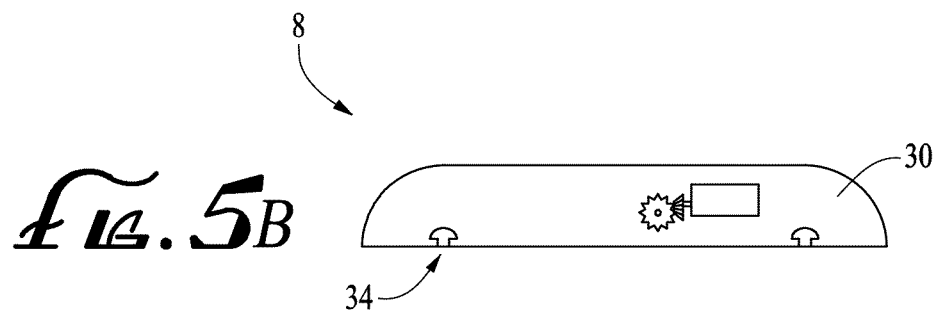
FIG. 5B illustrates a section view of a durable portion of a delivery device in accordance with an embodiment of the present invention.
Figure 5C:
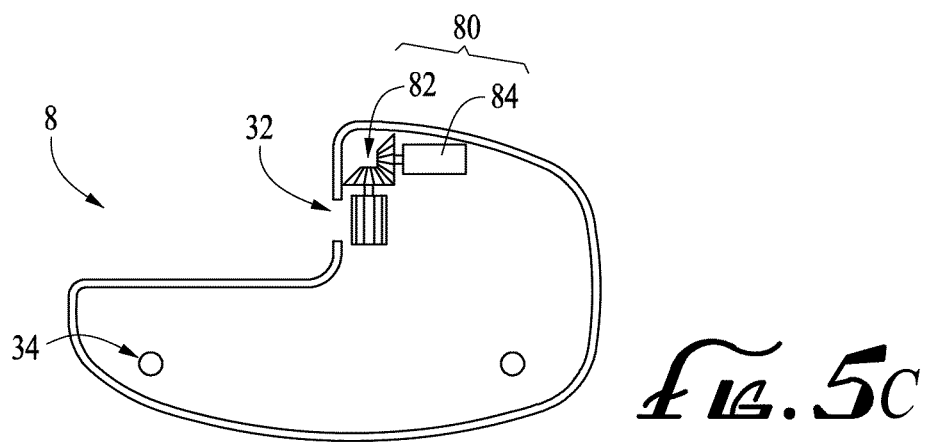
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 is configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
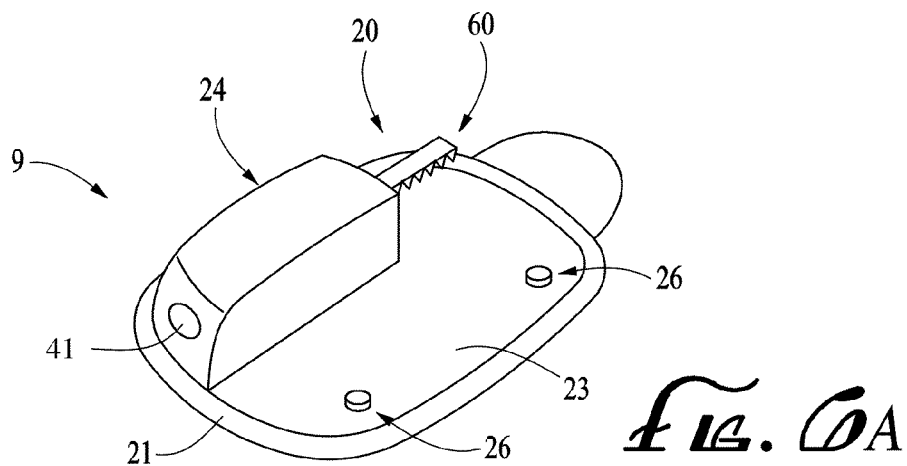
FIG. 6A illustrates a disposable portion of a delivery device in accordance with an embodiment of the present invention.
Figure 6B:
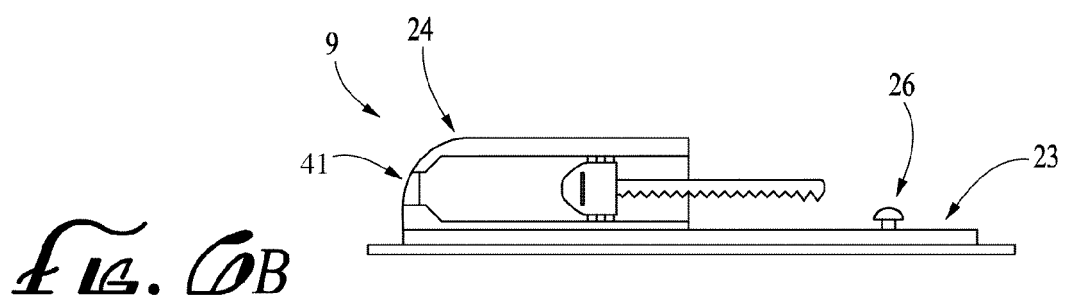
FIG. 6B illustrates a section view of a disposable portion of a delivery device in accordance with an embodiment of the present invention.
Figure 6C:
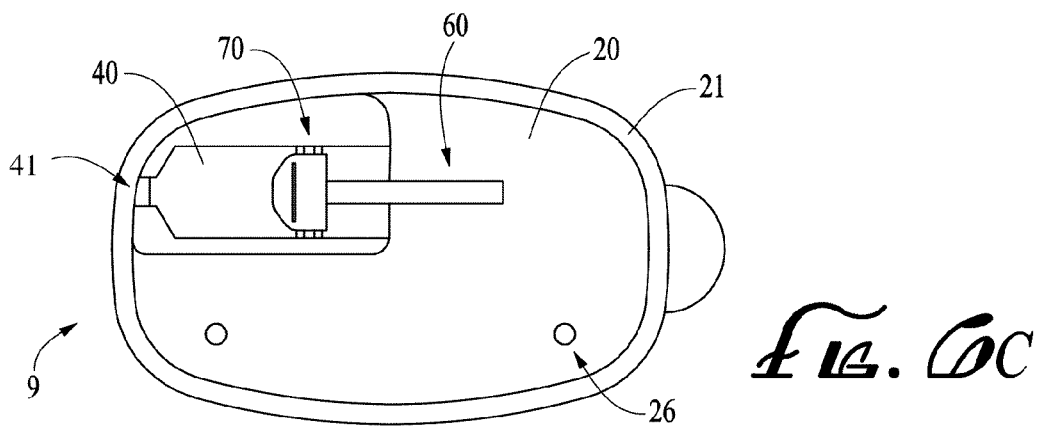
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir-retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. In addition, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir-retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

After the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry related to an amount of contents still remaining in the reservoir system 40. In some embodiments, the reservoir status circuitry is configured to store data to the reservoir circuitry, to update information in the reservoir circuitry related to an amount of contents remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

FIGS. 7-12 illustrate a reservoir system 100 that may be employed as an embodiment of the reservoir system 40 discussed above, for delivering fluidic media in accordance with an embodiment of the present invention. Although the reservoir system 100 may be similar or used with the embodiments of FIGS. 1-6C, it should be understood that the reservoir system 100 may also include some or all of the same components and operate in a manner similar to that shown and described in the embodiments of FIGS. 13-15B. In addition, some or all of the features shown in FIGS. 1-6C and 13-15B may be combined in various ways and included in the embodiment shown in FIGS. 7-12. The reservoir system 100 may include, but is not limited to, a container or body 110 of the reservoir, a plunger head 120, a plunger arm 126, and a plunger arm casing 130.

The reservoir body 110 may have an interior volume 112 for containing fluidic media. The reservoir body 110 may have a first port 114 for allowing fluidic media to flow into the interior volume 112 of the reservoir body 110. The reservoir body 110 may have a second port 116 for expelling fluidic media contained in the interior volume 112 of the reservoir body 110. In various embodiments, one of the first port 114 and the second port 116 of the reservoir body 110 may be for allowing fluidic media to flow into the interior volume 112 of the reservoir body 110 and for expelling fluidic media contained in the interior volume 112 of the reservoir body 110. In various embodiments, the reservoir body 110 may be made of various suitable materials, including, but not limited to, glass, plastic, TOPAS® polymers (or any other cyclic olefin copolymer (or polymer)), or the like.

The plunger head 120 may be located within the reservoir body 110 and may be moveable in an axial direction of the reservoir body 110 to expand (e.g., FIG. 7A) or contract (e.g., FIG. 7B) the interior volume 112 of the reservoir body 110. The plunger head 120 may be advanced within the reservoir body 110 to expel fluidic media contained in the interior volume 112 of the reservoir body 110 out the second port 116 of the reservoir body 110. The plunger head 120 may be made of Bromobutyl rubber, silicone rubber, or any other suitable material and/or any derivative thereof. The plunger head 120 may have a front portion 122 and a rear portion 123.

The front portion 122 of the plunger head 120 may be in contact with fluidic media contained in the interior volume 112 of the reservoir body 110. In some embodiments, the front portion 122 of the plunger head 120 may comprise a material compatible with fluidic media contained in the interior volume 112 of the reservoir body 110. In such embodiments, any number of the remaining portions of the plunger head 120, such as the rear portion 123 of the plunger head 120, the plunger arm 126, and the plunger arm casing 130 may be made of a similar material or of any suitable material, including, but not limited to, materials that need not be compatible with fluidic media contained in the interior volume 112 of the reservoir body 110. Such materials may be selected based on strength, cost, or the like.

In some embodiments, where the interior volume 112 of the reservoir body 110 is for containing insulin, the front portion 122 of the plunger head 120 may comprise an insulin compatible material, such as, but not limited to, polyethylene, or the like. In such embodiments, any number of the remaining portions of the plunger head 120, such as the rear portion 123 of the plunger head 120, the plunger arm 126, and the plunger arm casing 130, may be made of an insulin compatible material, which may be the same or different from that of the front portion 122, or of any suitable material, including, but not limited to, materials that need not be compatible with insulin.

In some embodiments, the front portion 122 of the plunger head 120 may be removably attachable to the plunger head 120 (or the rear portion 123). For example, the front portion 122 of the plunger head 120 may have one or more tabs 121 configured to fit into one or more apertures (not shown) located on the plunger head 120. Alternatively, the front portion 122 of the plunger head 120 may have one or more apertures (not shown) for receiving one or more tabs (not shown) provided on the plunger head 120 (or the rear portion 123). In various embodiments, the front portion 122 of the plunger head 120 may be secured to the plunger head 120 in any suitable manner, such as, but not limited to, a snap-fitting, an adhesive, friction fitting, laser welding, magnetic coupling, or the like.

The rear portion 123 of the plunger head 120 may be connected or connectable to an end of the plunger arm 126 in any suitable manner. For example, the rear portion 123 of the plunger head 120 may include an aperture (not shown) for receiving a tab (not shown) or the like of the plunger arm 126. The tab (not shown) may be snap-fit into the aperture (not shown) to connect the plunger arm 126 to the rear portion 123 of the plunger head 120. Alternatively, the rear portion 123 of the plunger head 120 may have one or more tabs (not shown) configured to fit into one or more apertures (not shown) located on the plunger arm 126. In various other embodiments, the plunger arm 126 may be connected to the plunger head 120 and/or the rear portion 123 of the plunger head 120 in any suitable manner, such as, but not limited to, an adhesive, friction fitting, laser welding, magnetic coupling, or the like.

The plunger arm 126 may be moveable in an axial direction within the plunger arm casing 130 and the reservoir body 110. In some embodiments, the plunger arm 126 and the rear portion 123 of the plunger head 120 may be integral to one another. In other embodiments, the plunger arm 126 and the rear portion 123 of the plunger head 120 may be separate components.

The plunger arm 126 may include an engagement side 128 for operatively engaging a drive member 140, drive linkage, or the like. For example, the engagement side 128 of the plunger arm 126 and the drive member 140 may be complementing gears, complementing threaded members, or the like, that may operatively engage one another. The drive member 140 may be a drive screw, drive rack, or the like. The drive member 140 may be connected to a motor (not shown) to move the drive member 140 to cause the plunger arm 126 to move within the plunger arm casing 130 and the reservoir body 110. Accordingly, the drive motor may actuate the plunger arm 126 to move within the reservoir body 110 to expand and contact the interior volume 112 of the reservoir body 110.

The plunger arm casing 130 may be for supporting the plunger arm 126 as the plunger arm 126 is moved along the plunger arm casing 130. At least one side of the plunger arm 126 may be in contact with one or more interior sides of the plunger arm casing 130. In some embodiments, the plunger arm casing 130 may be for aligning the plunger arm 126 as the plunger arm 126 is moved along the reservoir body 110, for example by the drive member 140. The plunger arm casing 130 may ensure linear alignment of the plunger arm 126 relative to the longitudinal axis of the reservoir body 110 and/or perpendicularity of the plunger head 120 relative to the reservoir body 110 as the plunger arm 126 and/or the plunger head 120 enters and/or moves within the reservoir body 110.

In various embodiments, the plunger arm casing 130 may be sized and configured to substantially envelop the plunger arm 126, for example in a case where the plunger head 120 is in a position substantially near the back end of the reservoir body 110 (e.g., FIG. 7A). Accordingly, the plunger head 120 may be moveable from that position toward a front end of the reservoir body 110 (e.g., FIG. 7B) in which case a portion of the plunger arm 126 may be located within the reservoir body 110 and a further portion of the plunger arm 126 may be located within the plunger arm casing 130. Thus in some embodiments, the plunger arm 126 may be located within the reservoir body 110 and/or the plunger arm casing 130 during use of the reservoir system 100 by the user-patient (e.g., during delivery of fluidic media to the user-patient).

Figure 8:
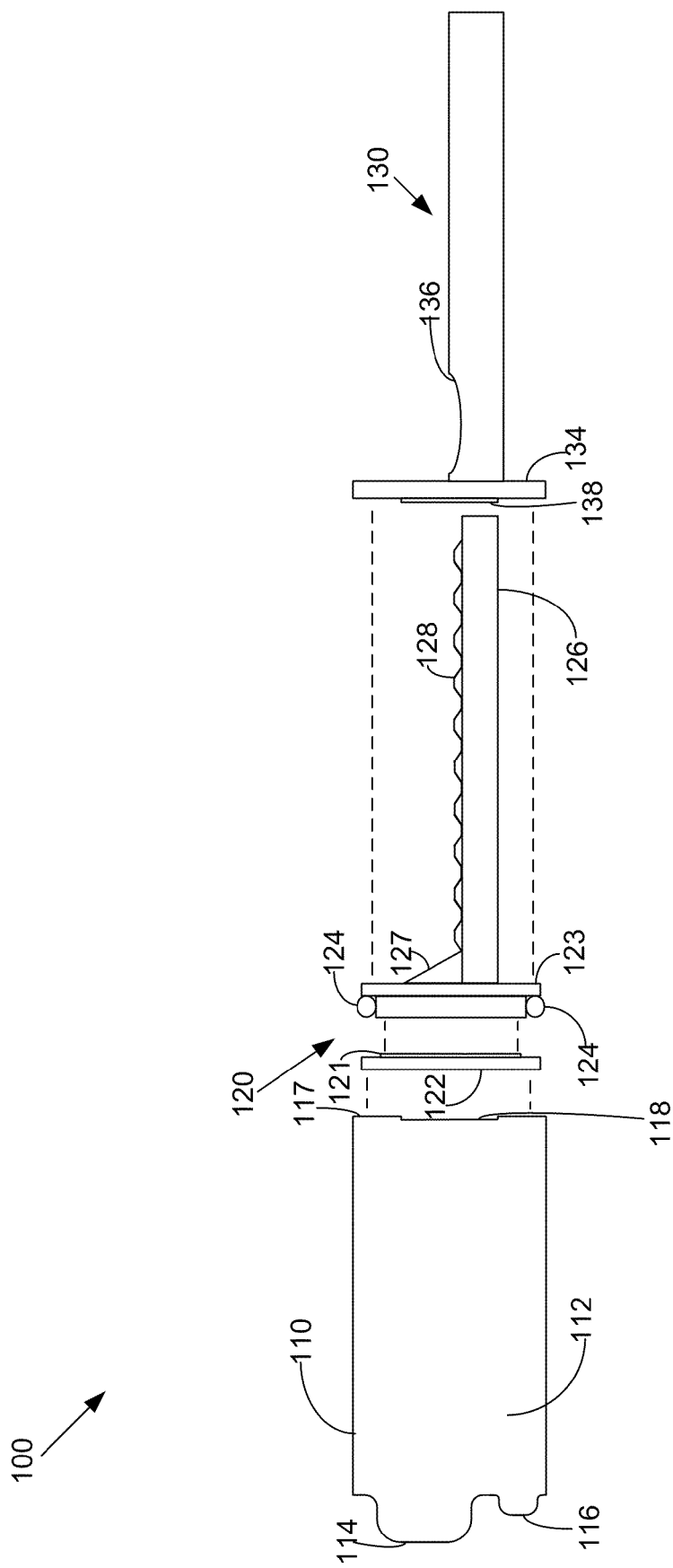
FIG. 8 illustrates an exploded view of a system for transferring fluidic media in accordance with an embodiment of the present invention.

With reference to FIGS. 7A, 7B, and 8, in some embodiments, the plunger arm casing 130 may have a feature such as an opening 136 for allowing a portion of the engagement side 128 of the plunger arm 126 to operatively engage the drive member 140. In such embodiments, the plunger arm 126 may be surrounded by the plunger arm casing 130 and/or the reservoir body 110. Accordingly in such embodiments, only the portion of the engagement side 128 of the plunger arm 126 exposed by the opening 136 may be free from (i.e., not covered by) the plunger arm casing 130 and/or the reservoir body 110 for operable engagement with the drive member 140. This may allow the drive member 140 to operatively engage the engagement side 128 of the plunger arm 126 while the plunger arm 126 or a portion thereof remains in the plunger arm casing 130 and/or the reservoir body 110.

The reservoir system 100 may include a reservoir cover (or casing) 134 that may be sized and configured to cover an end 117 of the reservoir body 110. For example, in a case where the first port 114 and the second port 116 is located on a first end of the reservoir body 110, a second end opposite the first end may be the end 117 of the reservoir body 110 covered by the reservoir cover 134. The reservoir cover 134 may be integral with the plunger arm casing 130.

In other embodiments, the reservoir cover 134 may be separate from the plunger arm casing 130. For example, the reservoir cover 134 may be removably attachable to the plunger arm casing 130. In such embodiments, the reservoir cover 134 may be connected to or connectable to the plunger arm casing 130 in any suitable manner, such as those previously described.

In some embodiments, the end 117 of the reservoir body 110 may be open. The reservoir cover 134 may cover the open end 117 of the reservoir body 110 or be configured to fit within the open end 117 of the reservoir body 110 to seal or close the open end 117 of the reservoir body 110. The open end 117 may allow the plunger head 120 and/or at least a portion of the plunger arm 126 attached to the plunger head 120 to be insertable into the reservoir body 110, for example, before the reservoir cover 134 is placed in/on the reservoir body 110 to cover the open end 117 of the reservoir body 110.

For example, the reservoir cover 134 may include one or more tabs 138 sized and configured to fit within one or more recesses 118 on end 117 of the reservoir body 110, to fit the reservoir cover 134 to the reservoir body 110, to substantially close the reservoir body 110 after the plunger head 120 and/or at least a portion of the plunger arm 126 have been placed in the reservoir body 110. Alternatively, the reservoir cover 134 may include one or more recesses (not shown) for receiving one or more tabs (not shown) of the reservoir body 110 to fit the reservoir cover 134 to the reservoir body 110. However, the reservoir cover 134 may be connected to or connectable to the reservoir body in any suitable manner, such as those previously described.

In some embodiments, the reservoir cover 134 and/or the plunger arm casing 130 may be configured for minimizing an expansion of the reservoir body 110, for example, as pressure within the reservoir body 110 increases during use. In such embodiments, by fitting the reservoir cover 134 to the back of the reservoir body 110 in one or more dimensions, the reservoir cover 134 may help to retain a shape of the reservoir body 110.

A seal member 124 (524 in FIG. 13), such as an o-ring or the like, may be positioned between the reservoir body 110 and a portion of the plunger head 120. The interior volume 112 of the reservoir body 110 may be on one side of the seal member 124. The reservoir body 110 may have a chamber 152 located on an opposite side of the seal member 124 from the interior volume 112 of the reservoir body 110.

The seal member 124 may be for substantially preventing fluidic media from flowing from the interior volume 112 of the reservoir body 110 to the chamber 152 of the reservoir body 110. The chamber 152 of the reservoir body 110 may be located between the seal member 124 and the reservoir cover 134 in a case where the plunger head 120 is in the reservoir body 110 and the reservoir cover 134 and/or the plunger arm casing 130 are fitted or otherwise attached to the reservoir body 110. In some embodiments, the seal member 124 may be located between the front portion 122 and the rear portion 123 of the plunger head 120.

In some embodiments, the reservoir system 100 may include at least one support flange 127 positioned on the plunger arm 126 and the rear portion 123 of the plunger head 120. The support flange 127 may provide additional structural strength to the plunger arm 126 and/or the plunger head 120. For example, the support flange 127 may have a triangular configuration and be positioned with one side of the support flange 127 connected to a top surface of the plunger arm 126 and a second side of the support flange 127 connected to the rear portion 123 of the plunger head 120. In addition or alternatively, a second support flange (not shown) may be positioned with one side of the second support flange (not shown) connected to a side surface of the plunger arm 126 and a second side of the second support flange (not shown) connected to the rear portion 123 of the plunger head 120.

In some embodiments, such as the embodiment illustrated in FIG. 9A, at least one of the one or more interior sides of the plunger arm casing 130 may include a plurality of protuberances 139 for contacting at least one side of the plunger arm 126. In other embodiments, such as the embodiment illustrated in FIG. 9B, the interior side of the plunger arm casing 130 may have a plurality of concavities and convexities 137. The convexities 137 may be for contacting at least one side of the plunger arm 126.

In some embodiments, such as the embodiment illustrated in FIG. 10A, the plunger arm 126 may have a plurality of protuberances 129 for contacting at least one interior side of the plunger arm casing (not shown) when at least a portion of the plunger arm 126 is in the plunger arm casing 130. In other embodiments, such as the embodiment illustrated in FIG. 10B, the plunger arm 126 may have a plurality of concavities and convexities 129. The convexities 129 may be for contacting at least one interior side of the plunger arm casing 130.

Figure 11:
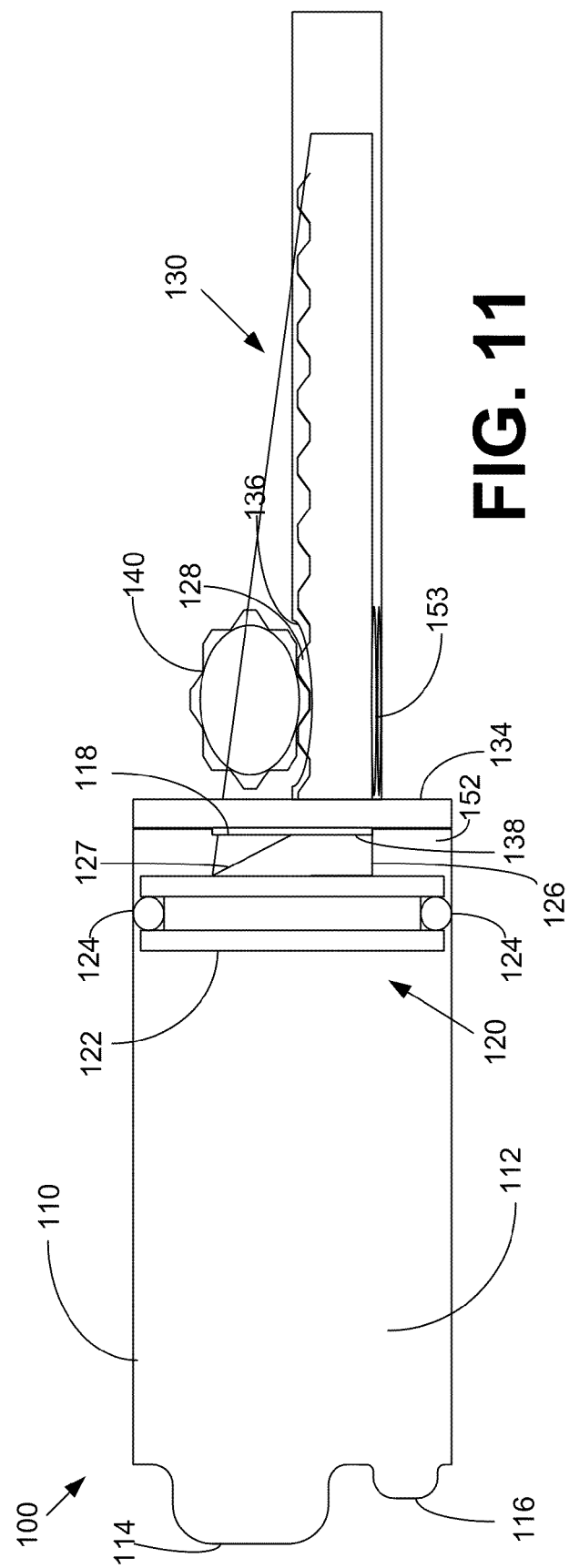
FIG. 11 illustrates a cross-section of a system for transferring fluidic media in accordance with an embodiment of the present invention.

In some embodiments, such as the embodiment illustrated in FIG. 11, the reservoir system 100 may include a bias member 153. The bias member 153 may comprise, but is not limited to, a spring or the like. The bias member 153 may be positioned between the plunger arm casing 130 and the plunger arm 126. The bias member 153 may be configured to force the plunger arm 126 against the drive member 140 to allow the plunger arm 126 to operatively engage the drive 140.

Figure 12:
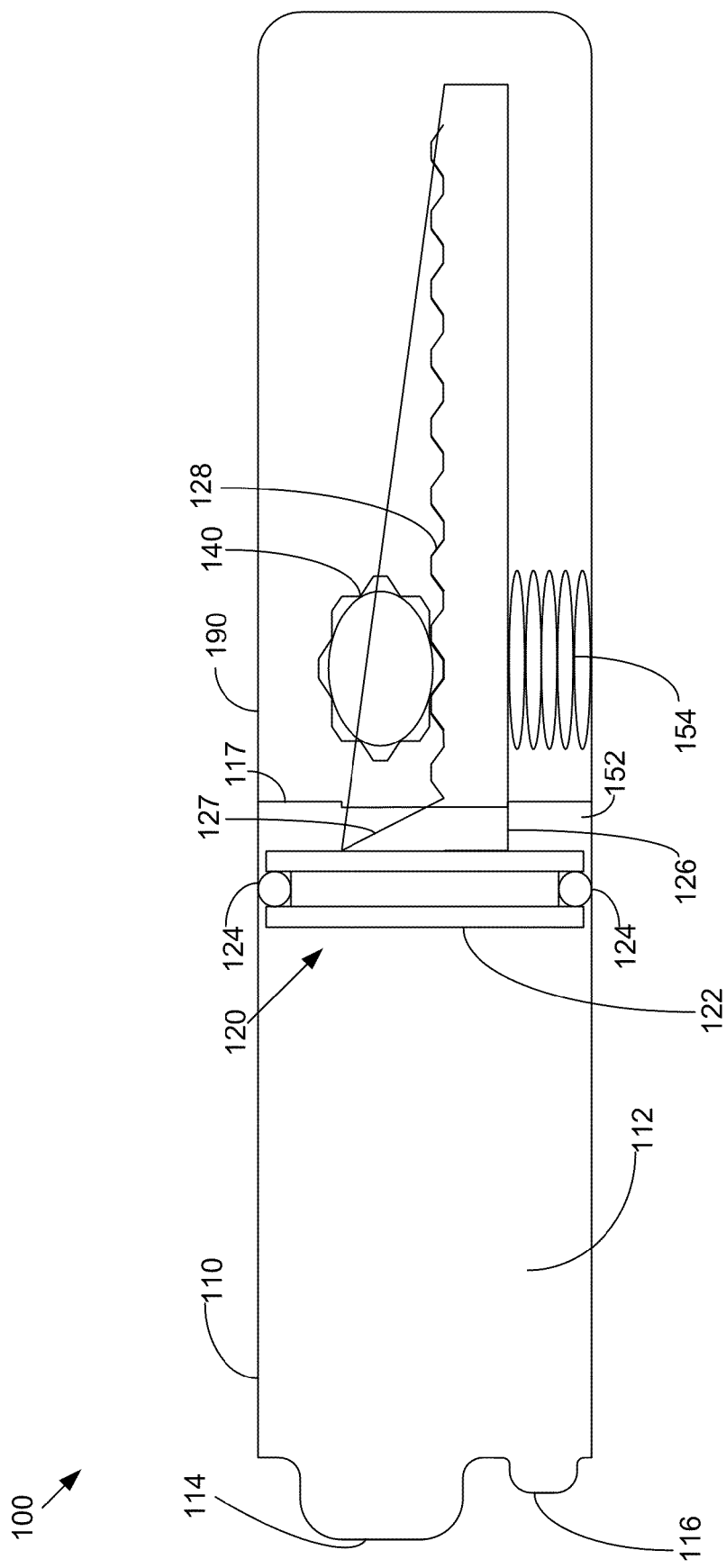
FIG. 12 illustrates a cross-section of a system for transferring fluidic media in accordance with an embodiment of the present invention.

In other embodiments, such as the embodiment illustrated in FIG. 12, the reservoir system 100 may include an outer casing 190 and a bias member 154. The outer casing 190 may be for enclosing at least a portion of the drive member 140 and at least a portion of the plunger arm 126. In various embodiments, the outer casing 190 may also enclose other drive components or portions thereof, such as, a drive motor (not shown) and/or other drive member(s)/linkage operatively connecting the drive member 140 and the drive motor (not shown).

The outer casing 190 be sized and configured to cover an end 117 of the reservoir body 110. For example, in a case where the first port 114 and the second port 116 is located on a first end of the reservoir body 110, a second end opposite the first end may be the end 117 of the reservoir body 110 covered by the reservoir cover 134. The outer casing 190 may cover the open end of the reservoir body 110 or have a portion adapted to fit within the open end of the reservoir body 110 to seal or close the open end of the reservoir body 110. In other embodiments, the outer casing 190 may be removably attachable to the plunger arm casing 130.

In some embodiments, the end 117 of the reservoir body 110 may be open. The outer casing 190 may cover the open end 117 of the reservoir body 110 or be configured to fit within the open end 117 of the reservoir body 110 to seal or close the open end 117 of the reservoir body 110. The open end 117 may allow the plunger head 120 and/or at least a portion of the plunger arm 126 attached to the plunger head 120 to be insertable into the reservoir body 110, for example, before the outer casing 190 is placed in/on the reservoir body 110 to cover the open end 117 of the reservoir body 110.

For example, the outer casing 190 may include one or more tabs 138 sized and configured to fit within one or more recesses 118 on end 117 of the reservoir body 110, to fit the outer casing 190 to the reservoir body 110, to substantially close the reservoir body 110 after the plunger head 120 and/or at least a portion of the plunger arm 126 have been placed in the reservoir body 110. Alternatively, the outer casing 190 may include one or more recesses (not shown) for receiving one or more tabs (not shown) of the reservoir body 110 to fit the outer casing 190 to the reservoir body 110. However, the outer casing 190 may be connected to or connectable to the reservoir body 110 in any suitable manner, such as those previously described.

The bias member 154 may comprise, but is not limited to, a spring or the like. The bias member 154 may be positioned between the outer casing 190 and the plunger arm 126. The bias member 154 may be configured to force the plunger arm 126 against the drive member 140 to allow the plunger arm 126 to operatively engage the drive 140.

In some embodiments, the reservoir system 100 may include a plunger arm casing (not shown) that may have an opening 136 for allowing a portion of the engagement side 128 of the plunger arm 126 to operatively engage the drive member 140. In such embodiments, the plunger arm 126 may be completely surrounded by the plunger arm casing (not shown) and/or the reservoir body 110. Accordingly, only the portion of the engagement side 128 of the plunger arm 126 exposed by the opening 136 may not be covered by the plunger arm casing (not shown) and/or the reservoir body 110, thus allowing the drive member 140 to operatively engage the engagement side 128 of the plunger arm 126. In further embodiments, the plunger arm casing (not shown) may be adapted to allow the bias member 154 to contact the plunger arm 126. For example, the plunger arm casing (not shown) may include a second opening for allowing the bias member 154 to contact the plunger arm 126.

In some embodiments, the outer casing 190 and/or the plunger arm casing 130 may be configured for minimizing an expansion of the reservoir body 110, for example, as pressure within the reservoir body 110 increases during use. In such embodiments, by fitting the outer casing 190 to the back of the reservoir body 110 in one or more dimensions, the outer casing 190 may help to retain a shape of the reservoir body 110.

In various embodiments where the reservoir system 100 is pre-filled with fluidic media, the reservoir 110 may include a plunger head (e.g., 120) that may be attachable to the delivery device (not shown) as described above. In other embodiments, the plunger head may be placed in the reservoir 110 before or after the reservoir 110 is filled with fluidic media.

FIG. 13 illustrates a reservoir system 500 that may be employed as an embodiment of the reservoir system 40 discussed above, for delivering fluidic media in accordance with an embodiment of the present invention. Although the reservoir system 500 may be similar or used with the embodiments of FIGS. 7-12, it should be understood that the reservoir system 500 may also include some or all of the same components and operate in a manner similar to that shown and described in the embodiments of FIGS. 1-6C and 13-15B. In addition, some or all of the features shown in FIGS. 1-12 and 13-15B may be combined in various ways and included in the embodiment shown in FIG. 13. The reservoir system 500 may include, but is not limited to, a reservoir 510, a plunger head 520, a plunger arm 526, and a seal member 524.

The reservoir 510 may have an interior volume 512 for containing fluidic media. The reservoir 510 may have a port 516 for expelling fluidic media contained in the interior volume 512 of the reservoir 510. In various embodiments, the reservoir 510 may be made of various suitable materials, including, but not limited to, glass, plastic, TOPAS® polymers (or any other cyclic olefin copolymer (or polymer)), or the like.

The plunger head 520 may be located within the reservoir 510 and may be moveable in an axial direction of the reservoir 510 to expand or contract the interior volume 512 of the reservoir 510. The plunger head 520 may be advanced within the reservoir 510 to expel fluidic media contained in the interior volume 512 of reservoir 510 out the port 516 of the reservoir 510. The plunger head 520 may be made of Bromobutyl rubber, silicone rubber, or any other suitable material and/or any derivative thereof.

The plunger head 520 may have a front portion 522 and a rear portion 523. The front portion 522 of the plunger head 520 may be in contact with fluidic media contained in the interior volume 512 of the reservoir 510. The rear portion 523 of the plunger head 520 may be connected or connectable to an end of the plunger arm 526 in any suitable manner.

A seal member 524, such as an o-ring, may be positioned between the reservoir 510 and the plunger head 520. The interior volume 512 of the reservoir 510 may be on one side of the seal member 524. The reservoir 510 may have a chamber 552 located on an opposite side of the seal member 524 from the interior volume 512 of the reservoir 510. The seal member 524 may be for substantially preventing fluidic media from flowing from the interior volume 512 of the reservoir body 110 to the chamber 552 of the reservoir 510. In some embodiments, the seal member 524 may be located between the front portion 522 and the rear portion 523 of the plunger head 520. The seal member 524 may be made of silicone, rubber, or any other suitable material for substantially preventing fluid from flowing between the reservoir 510 and the plunger head 520.

The seal member 524 may have a first end 524a and a second end 524b. The first end 524a of the seal member 524 and the second end 524b of the seal member 524 may taper towards each other to a mid-portion 525. The first end 524a of the seal member 524 and the second end 524b of the seal member 524 may each be substantially round and tapering to the mid-point 525. In some embodiments, the seal member 524 may have a peanut-shaped cross-section.

The first end 524a of the seal member 524 and the second end 524b of the seal member 524 may contact the reservoir 510. In some embodiments, a space may be located or otherwise formed between the mid-portion 525 of the seal member 524 and the reservoir 510, such that the mid-portion 525 of the reservoir 510 does not contact the reservoir body 110.

In various embodiments where the reservoir 510 is prefilled with fluidic media, the reservoir 510 may include a plunger head (e.g., 520) that may be attachable to the delivery device (not shown) as described above. In further embodiments, the plunger head may be placed in the reservoir 510 before or after the reservoir 510 is filled with fluidic media.

FIGS. 14A-15B illustrate reservoir systems 600 that may be employed as embodiments of the reservoir system 40 discussed above, for delivering fluidic media in accordance with an embodiment of the present invention. Although the reservoir system 600 may be similar or used with the embodiments of FIGS. 7-13, it should be understood that the reservoir system 600 may also include some or all of the same components and operate in a manner similar to that shown and described in the embodiments of FIGS. 1-6C. In addition, some or all of the features shown in FIGS. 1-13 may be combined in various ways and included in the embodiment shown in FIGS. 14A-15B. The reservoir system 600 may include, but is not limited to, a reservoir 610, a plunger head 620, a plunger arm 626, and a seal member 624.

The reservoir 610 may have an interior volume 612 for containing fluidic media. The reservoir 610 may have a port 616 for expelling fluidic media contained in the interior volume 612 of the reservoir 610. In various embodiments, the reservoir 610 may be made of various suitable materials, including, but not limited to, glass, plastic, TOPAS® polymers (or any other cyclic olefin copolymer (or polymer)), or the like.

The plunger head 620 may be located within the reservoir 610 and may be moveable in an axial direction of the reservoir 610 to expand or contract the interior volume 612 of the reservoir 610. The plunger head 620 may be advanced within the reservoir 610 to expel fluidic media contained in the interior volume 612 of reservoir 610 out the port 616 of the reservoir 610. The plunger head 620 may be made of Bromobutyl rubber, silicone rubber, or any other suitable material and/or any derivative thereof.

The plunger head 620 may have a front portion 622 and a rear portion 623. The front portion 622 of the plunger head 620 may be in contact with fluidic media contained in the interior volume 612 of the reservoir 610. The rear portion 623 of the plunger head 620 may be connected or connectable to an end of the plunger arm 626 in any suitable manner.

A seal member 624, such as an o-ring, may be positioned between the reservoir 610 and the plunger head 620. The interior volume 612 of the reservoir 610 may be on one side of the seal member 624. The reservoir 610 may have a chamber 652 located on an opposite side of the seal member 624 from the interior volume 612 of the reservoir 610. The seal member 624 may be for substantially preventing fluidic media from flowing from the interior volume 612 of the reservoir body 610 to the chamber 652 of the reservoir 610. The seal member 624 may be made of silicone, rubber, or any other suitable material for substantially preventing fluid from flowing between the reservoir 610 and the plunger head 620.

In some embodiments, the seal member 624 may be located at least partially between the front portion 622 and the rear portion 623 of the plunger head 620. The plunger head 620 may have a groove 625 surrounding a perimeter of the plunger head 620 with a first ridge 621a of the plunger head 620 and a second ridge 621b of the plunger head 620 defining the groove 625. The seal member 624 may be arranged at least partially in the groove 625 of the plunger head 620.

Protrusions 628 may be arranged or otherwise formed on the first ridge 621a and/or the second ridge 621b. The protrusions 628 may be for stabilizing the plunger head 620 as the plunger head 620 moves within the reservoir body 610. The protrusions 628 may stabilize the plunger head 620 by substantially preventing movement (e.g., pivotal or lateral movement) of the plunger head 620, for example, in directions M1 and M2. In other words, the protrusions may prevent excessive perpendicularity of the plunger head 620 relative to the reservoir body 610. The protrusions 628 may control compression of the seal member 624. The protrusions 628 on the first ridge 621a may or may not be aligned with the protrusions 628 on the second ridge 621b. The protrusions 628 may be formed on the plunger head 628 or may be attached to the plunger head, for example, with an adhesive, friction fit, or the like.

Figure 14A:
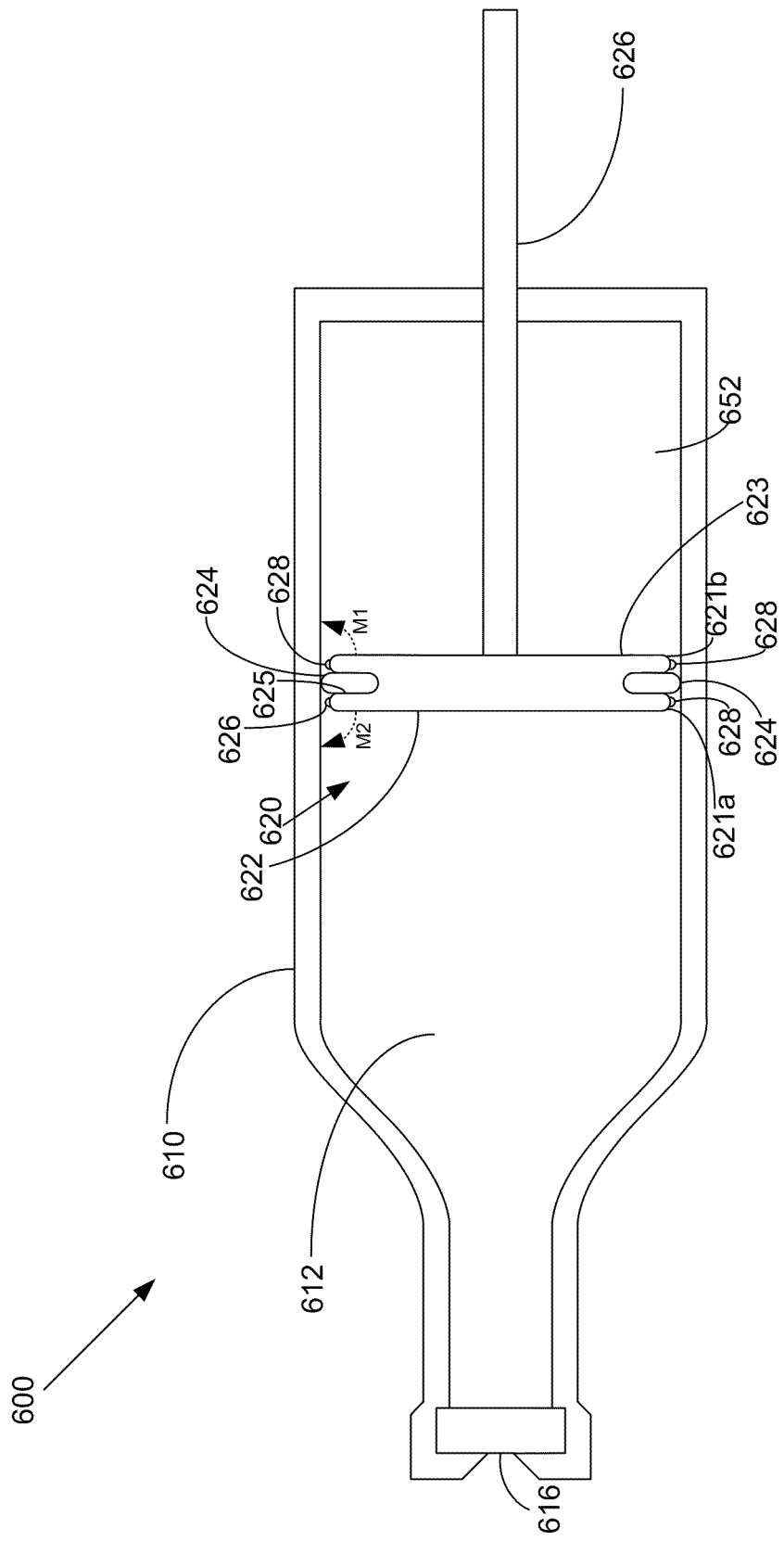
FIG. 14A illustrates a cross-section of a system for transferring fluidic media in accordance with an embodiment of the present invention.
Figure 14B:
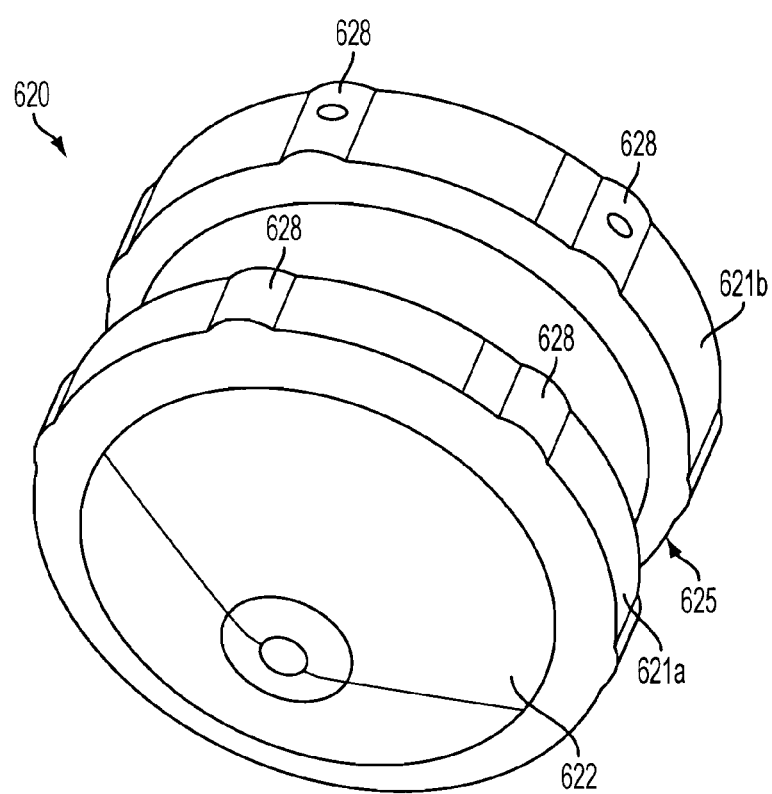
FIG. 14B illustrates a portion of a system for transferring fluidic media in accordance with an embodiment of the present invention.

In some embodiments, such as the embodiment exemplified in FIG. 14B, six protrusions 628 may be arranged equidistantly around each of the first ridge 621a and the second ridge 621b. However, in other embodiments, the protrusions 628 need not be so limited as the protrusions 628 may be arranged in any suitable manner. For example, the first ridge 621a and/or the second ridge 621b may have any number of protrusions 628; the first ridge 621a and the second ridge 621b need not have equal number of protrusions 628; the first ridge 621a and the second ridge 621b may each extend different distances from the plunger head 620; and/or each protrusion 628 need not be equidistant from each other.

In some embodiments, the protrusions 628 may extend a distance D away from the first ridge 621a and/or the second ridge 621b and the seal member 624 may extend a distance 2D beyond the first ridge 621a and/or the second ridge 621b. In further embodiments, D may be selected based on the reservoir body 610 selected. In other embodiments, the protrusions 628 and/or the seal member 624 may extend beyond the first ridge 621a and/or the second ridge 621b any suitable distance.

Figure 15A:
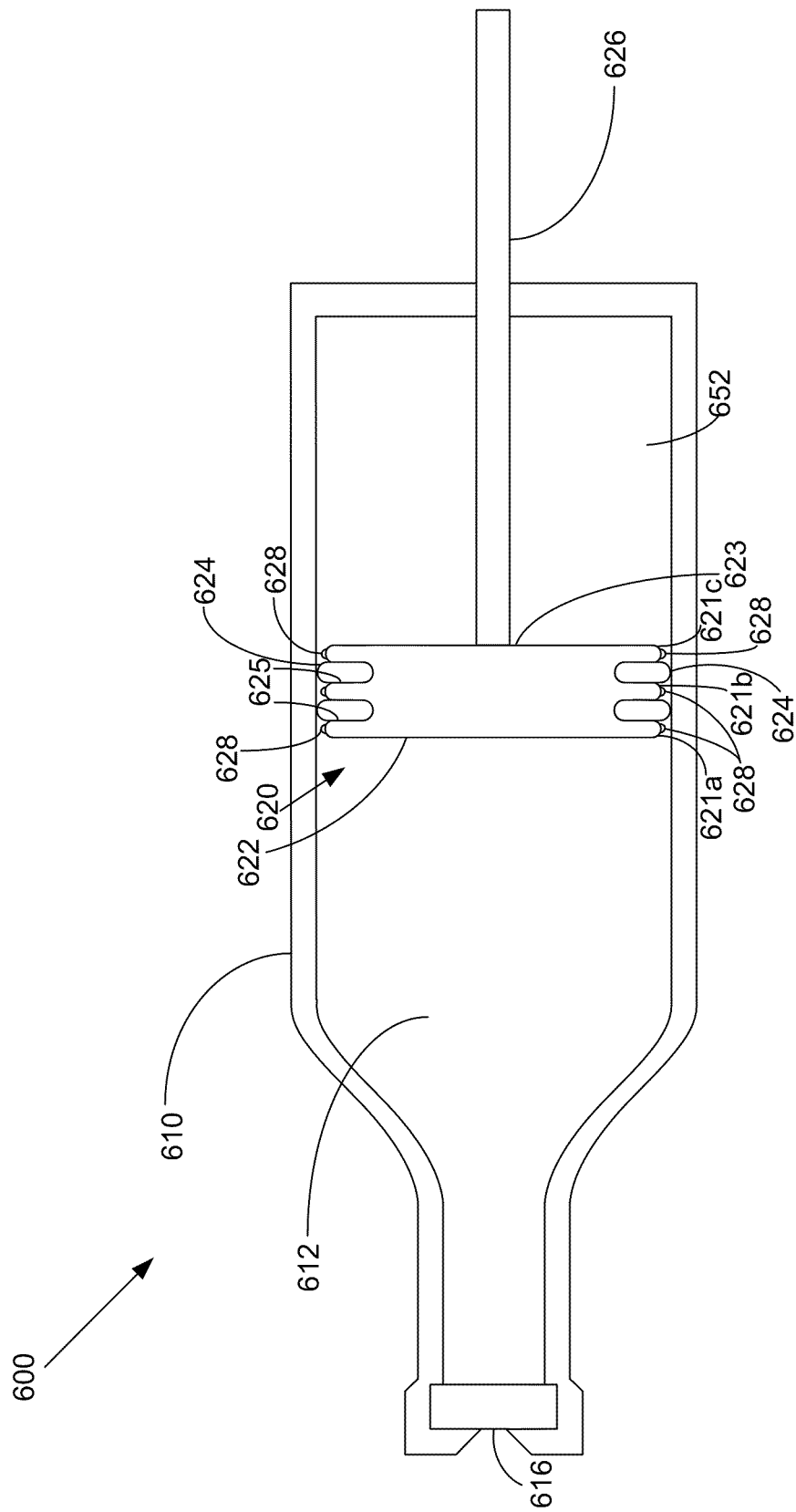
FIG. 15A illustrates a cross-section of a system for transferring fluidic media in accordance with an embodiment of the present invention.
Figure 15B:
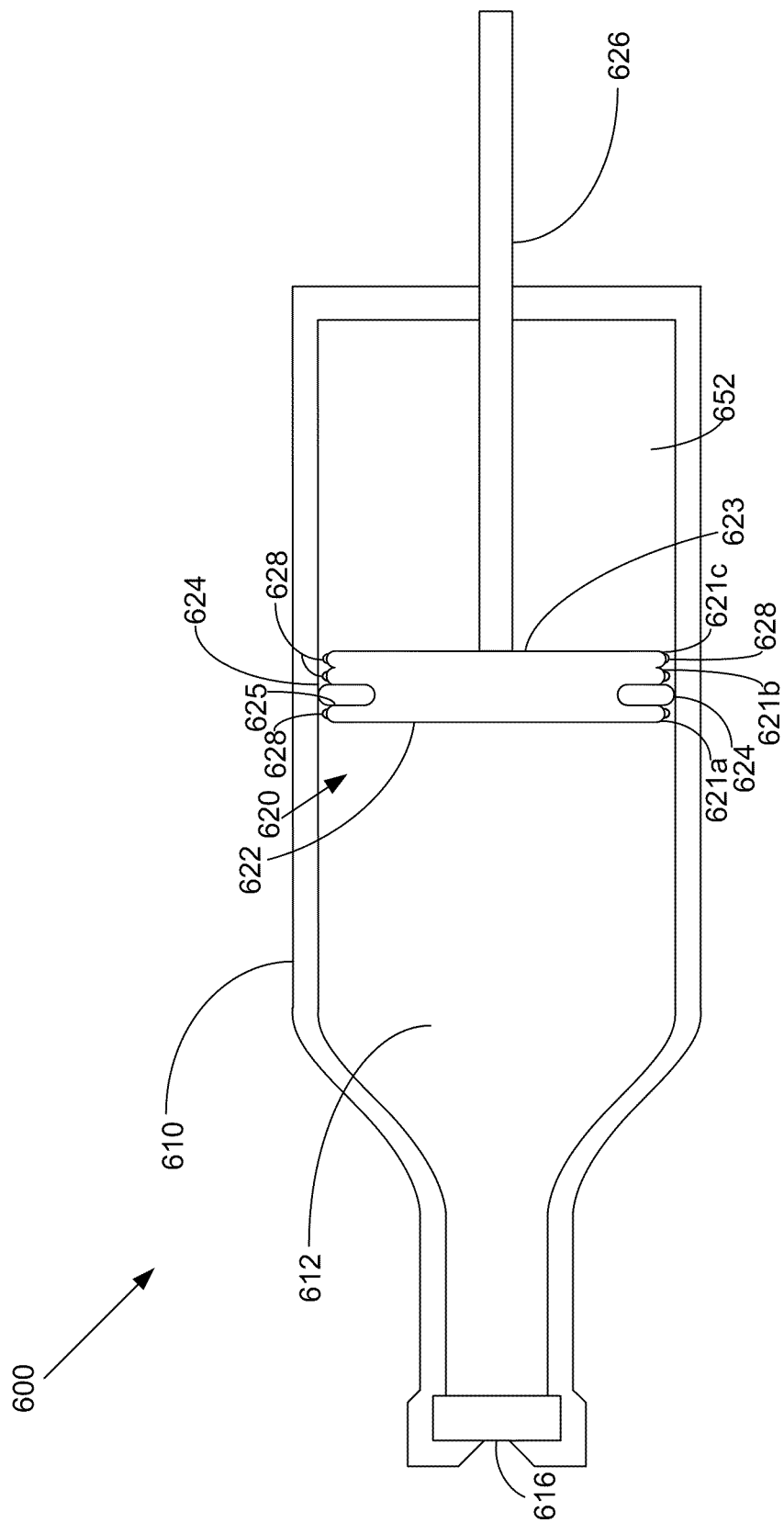
FIG. 15B illustrates a cross-section of a system for transferring fluidic media in accordance with an embodiment of the present invention.

In some embodiments, the plunger head 620 may include additional ridges 621c-621n each separated by a groove 625 containing a seal member 624, as exemplified in FIG. 15A. Any of the additional ridges 621c-621n may include protrusions 628 as previously described. In some embodiments, each or some of the first ridge 621a, the second ridge 621b, and/or the additional ridges 621c-621n need not be separated by a groove 625 and/or a seal member 624. For example, a second ridge 621b and a third ridge 621c may be adjacent to each other with a seal member 624 arranged between the first ridge 621a and the second ridge 621b, as exemplified in FIG. 15B.

In various embodiments where the reservoir 610 is prefilled with fluidic media, the reservoir 610 may include a plunger head (e.g., 620) that may be attachable to the delivery device (not shown) as described above. In further embodiments, the plunger head may be placed in the reservoir 610 before or after the reservoir 610 is filled with fluidic media.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for transferring fluidic media, the system comprising:
    a reservoir body having an interior volume for containing fluidic media and an opening;
    a plunger head moveable in an axial direction within the reservoir body;
    a plunger arm operatively connected to the plunger head, the plunger arm having an arm portion extending out of the opening of the reservoir body for operatively engaging a drive member configured to move the plunger arm and the plunger head relative to the reservoir body when the arm portion is operatively engaged to the drive member;
    a reservoir cover covering at least a portion of the opening of the reservoir body; and
    a casing concentrically surrounding the plunger arm for supporting or aligning the plunger arm, wherein the casing is fixed to the reservoir cover so as to extend from the reservoir cover along the axial direction to allow the plunger arm to move in the axial direction relative to the casino and the reservoir body to move the plunger head in the axial direction within the reservoir body.

2. The system of claim 1, the plunger arm having at least one side adjacent the casing and at least partially supported by the casing to align the plunger arm for movement in the axial direction relative to the reservoir body.

3. The system of claim 2, the plunger arm having at least two sides adjacent the casing and at least partially supported by the casing to align the plunger arm for movement in the axial direction relative to the reservoir body, the at least two sides comprising a first side and a second side opposite the first side, the first side and the second side parallel the axial direction.

4. The system of claim 1, the casing having an opening for allowing the arm portion of the plunger arm to operatively engage the drive member through the opening.

5. The system of claim 4, the opening for allowing a mating portion of the drive member to extend through the opening to operatively engage the arm portion of the plunger arm within the interior of the casing.

6. The system of claim 1, further comprising a plurality of protuberances positioned on a surface of the plunger arm, the protuberances on the surface of the plunger arm for contacting an interior surface of the casing.

7. The system of claim 1, the plunger arm having a surface having concavities and convexities, the convexities on the surface of the plunger arm for contacting an interior surface of the casing.

8. The system of claim 1, further comprising a plurality of protuberances positioned on an interior surface of the casing, the protuberances on the interior surface of the casing for contacting the plunger arm.

9. The system of claim 1, the casing having an interior surface having concavities and convexities, the convexities on the interior surface of the casing for contacting the plunger arm.

10. The system of claim 1, further comprising a support flange having a first side and a second side, the first side of the support flange connected to a side of the plunger arm, the second side of the support flange connected to a surface of the plunger head that is operatively connected to the plunger arm.

11. The system of claim 1, wherein the plunger arm is fully enclosed within the interior of the casing.

12. The system of claim 1, the system further comprising a bias member supported in the interior of the casing to be between a wall of the casing and the plunger arm, the bias member configured to force the plunger arm against the drive member to operatively engage the plunger arm to the drive member.

13. The system of claim 1, the casing configured to fit in the end of the reservoir body.

14. The system of claim 1, the easing having a mating portion for mating with a mating portion of the end of the reservoir body.

15. The system of claim 1,
    the easing having a width dimension and a thickness dimension transverse to each other;
    the reservoir body having a width dimension and a thickness dimension transverse to each other, the width dimension and the thickness dimension of the reservoir body transverse the axial direction;
    wherein the width dimension and the thickness dimension of the reservoir body are each equal to or greater than the width dimension and the thickness dimension of the casing, respectively.

16. The system of claim 1,
the reservoir body having a port for transferring fluidic media contained in the interior volume;
the interior volume defined by a reservoir wall and an end of the reservoir body, the end of the reservoir body opposite the port of the reservoir body;
the plunger head arranged in the interior volume between the end and the port of the reservoir to be moveable in the axial direction within interior volume of the reservoir body;
the easing connected to the end of the reservoir body so as to extend from the reservoir body along the axial direction to allow the plunger arm to move in the axial direction relative to the reservoir body to move the plunger head in the axial direction within the reservoir body.

17. The system of claim 1, wherein the casing is integral with the reservoir cover.

18. A method of making a system for transferring fluidic media, the method comprising:
providing a reservoir body having an interior volume for containing fluidic media;
locating a plunger head moveable in an axial direction within the reservoir body;
operatively connecting a plunger arm to the plunger head, the plunger arm having an arm portion extending out of an opening of the reservoir body for operatively engaging a drive member configured to move the plunger arm and the plunger head relative to the reservoir body when the arm portion is operatively engaged to the drive member; and
supporting concentrically the plunger arm for movement in an interior of a casing and relative to the casing, the casing supporting or aligning the plunger arm, wherein the casing is fixed to a reservoir cover covering at least a portion of the opening of the reservoir body so as to extend from the reservoir cover along the axial direction to allow the plunger arm to move in the axial direction relative to the casing and the reservoir body to move the plunger head in the axial direction within the reservoir body.

19. A system for transferring fluidic media, the system comprising:
a reservoir having an interior volume for containing fluidic media and an opening;
a reservoir cover covering at least a portion of the opening;
a plunger head enclosed within the reservoir, the plunger head moveable in an axial direction within the reservoir, the plunger head comprising:
a front portion in contact with fluidic media when fluidic media is in the interior volume of the reservoir, the front portion comprising a first material compatible with fluidic media in the interior volume of the reservoir;
a rear portion located on an opposite side of the plunger head from the interior volume of the reservoir, the rear portion connectable to a plunger arm, the rear portion comprising a second material different from the first material, the second material incompatible with the fluidic media in the interior volume of the reservoir, wherein the plunger arm extends out of the opening of the reservoir and is concentrically surrounded by a casing, which is fixed to the reservoir cover, the casing for supporting or aligning the plunger arm, the plunger arm being moveable relative to the casing.

20. The system according to claim 19, further comprising a seal member positioned between the reservoir and the plunger head.

21. The system according to claim 20, the seal member positioned between the front portion and the rear portion of the plunger head.

22. The system according to claim 19, further comprising a connection structure that removably attaches the front portion of the plunger head to the rear portion of the plunger head and allows removal of the front portion of the plunger head from the rear portion of the plunger head.

23. The system according to claim 19, wherein the front portion of the plunger head has a diameter that is substantially equal to a diameter of the rear portion of the plunger head.

24. The system of claim 23, wherein the diameter of the front portion of the plunger head is equal to the diameter of the rear portion of the plunger head.

25. The system according to claim 19, wherein the front portion and the rear portion of the plunger head is are each entirely enclosed in the reservoir.

26. The system of claim 19, the front portion and the rear portion of the plunger head each having a thickness dimension extending in the axial direction, the reservoir body having a thickness dimension extending in the axial direction, the thickness dimensions of the reservoir body greater than the front portion and the rear portion of the plunger head collectively.

27. A method of making a system for transferring fluidic media, the method comprising:
providing a reservoir having an interior volume for containing fluidic media and an opening, wherein the opening is covered by a reservoir cover;
locating a plunger head enclosed within the reservoir, the plunger head moveable in an axial direction within the reservoir, the plunger head having a front portion and a rear portion, the from portion in contact with fluidic media when fluidic media is in the interior volume of the reservoir, the front portion comprising a first material compatible with fluidic, media in the interior volume of the reservoir, the rear portion located on an opposite side of the plunger head from the interior volume of the reservoir, the rear portion connectable to a plunger arm, the rear portion comprising a second material different from the first material, the second material incompatible with the fluidic media in the interior volume of the reservoir, wherein the plunger arm extends out of the opening of the reservoir and is concentrically surrounded by a casing, which is fixed to the reservoir cover, the casing for supporting or aligning the plunger arm, the plunger arm being moveable relative to the casing.

28. A system for transferring fluidic media, the system comprising:
a plunger arm operatively connectable to a plunger head that is moveable in an axial direction within a reservoir, the plunger arm having an arm portion extending out of an opening of the reservoir body and that is configured for operative engagement to a drive member configured to move the plunger arm and the plunger head when the arm portion of the plunger arm is operatively engaged to the drive member;
a casing concentrically surrounding the plunger arm for supporting or aligning the plunger arm, wherein the casing is fixed to a reservoir cover covering at least a portion of a reservoir opening so as to extend from the reservoir cover along the axial direction to allow the plunger arm to move in the axial direction relative to the casing and the reservoir body to move the plunger head in the axial direction within the reservoir body; and a bias member operatively engaged with the casing, the bias member configured to force the plunger arm against the drive member to operatively engage the plunger arm to the drive member.

29. The system of claim 28, the bias member positioned between the casing and the plunger arm.

30. The system of claim 28, the easing having an opening for allowing the arm portion of the plunger arm to operatively engage the drive member.

31. The system of claim 30, the opening for allowing a mating portion of the drive member to extend through the opening to operatively engage the arm portion of the plunger arm within the interior of the casing.

32. The system of claim 28, further comprising an outer casing configured to enclose at least a portion of the drive member and at least a portion of the plunger arm.

33. The system of claim 32, the bias member positioned between the outer casing and the plunger arm.

34. A method of making a system for transferring fluidic media, the method comprising:

providing a plunger arm operatively connectable to a plunger head that is moveable in an axial direction within a reservoir, the plunger arm having an arm portion extending out of an opening of the reservoir body and that is configured liar operative engagement to a drive member configured to move the plunger arm and the plunger head when the arm portion of the plunger arm is operatively engaged to the drive member;

providing a casing concentrically surrounding the plunger arm for supporting or aligning the plunger arm, wherein the casing is fixed to a reservoir cover covering at least a portion of an opening of the reservoir so as to extend from the reservoir cover along the axial direction to allow the plunger arm to move in the axial direction relative to the casing and the reservoir body to move the plunger head in the axial direction within the reservoir body; and providing a bias member operatively engaged with the casing, the bias member configured to force the plunger arm against the drive member to operatively engage the plunger arm to the drive member.

* * * * *